(12) United States Patent
Ideue et al.

(10) Patent No.: US 11,759,405 B2
(45) Date of Patent: Sep. 19, 2023

(54) COMPOSITION FOR ORAL CAVITY

(71) Applicant: SUNSTAR SUISSE SA, Etoy (CH)

(72) Inventors: Taku Ideue, Osaka (JP); Akihiko Komine, Osaka (JP); Ryotaro Nishioka, Osaka (JP); Shuhei Ishii, Osaka (JP)

(73) Assignee: SUNSTAR SUISSE SA, Etoy (CH)

( * ) Notice: Subject to any disclaimer, the term of this patent is extended or adjusted under 35 U.S.C. 154(b) by 0 days.

(21) Appl. No.: 17/417,305

(22) PCT Filed: Dec. 27, 2019

(86) PCT No.: PCT/JP2019/051625
§ 371 (c)(1),
(2) Date: Jun. 22, 2021

(87) PCT Pub. No.: WO2020/138500
PCT Pub. Date: Jul. 2, 2020

(65) Prior Publication Data
US 2022/0071853 A1  Mar. 10, 2022

(30) Foreign Application Priority Data

Dec. 27, 2018 (JP) ................... 2018-245027
Jun. 28, 2019 (JP) ................... 2019-121902
(Continued)

(51) Int. Cl.
*A61K 6/838* (2020.01)
*A61K 6/17* (2020.01)
(Continued)

(52) U.S. Cl.
CPC ............. *A61K 6/838* (2020.01); *A61K 6/17* (2020.01); *A61K 8/19* (2013.01); *A61K 8/21* (2013.01);
(Continued)

(58) Field of Classification Search
CPC . A61K 6/838; A61K 6/17; A61K 8/19; A61K 8/21; A61K 8/25; A61K 8/26;
(Continued)

(56) References Cited

U.S. PATENT DOCUMENTS

| 4,988,499 A | 1/1991 | Bristow et al. |
| 2010/0166678 A1 | 7/2010 | Iida et al. |
| 2015/0202128 A1* | 7/2015 | Saito ............ A61Q 11/00 424/57 |

FOREIGN PATENT DOCUMENTS

| EP | 0346957 A1 | 12/1989 |
| EP | 3904281 A1 | 11/2021 |

(Continued)

OTHER PUBLICATIONS

Kim et al., Synthesis of calcium-deficient hydroxyapatite in the presence of amphiphilic triblock copolymer, Materials Letters, Aug. 24, 2011, pp. 33-35, Elsevier.
(Continued)

*Primary Examiner* — Adam C Milligan
*Assistant Examiner* — Amanda Michelle Petritsch
(74) *Attorney, Agent, or Firm* — Paratus Law Group, PLLC

(57) ABSTRACT

Provided is an oral composition containing particles that have properties to seal dentinal tubules and excellent adhesion properties in dentinal tubules. Specifically, provided is an oral composition containing hydroxyapatite particles, wherein the hydroxyapatite particles have a ratio of a diffraction peak intensity around $2\theta=32°$ to a diffraction peak intensity around $2\theta=26°$ of 0.8 to 1.6 in an x-ray powder diffraction pattern as measured with CuKα characteristic X-rays.

9 Claims, 14 Drawing Sheets

(30) Foreign Application Priority Data

Jun. 28, 2019 (JP) ................................ 2019-121905
Jun. 28, 2019 (JP) ................................ 2019-121912
Jun. 28, 2019 (JP) ................................ 2019-121916

(51) Int. Cl.

| A61K 8/19 | (2006.01) |
|---|---|
| A61K 8/21 | (2006.01) |
| A61K 8/25 | (2006.01) |
| A61K 8/26 | (2006.01) |
| A61Q 11/00 | (2006.01) |

(52) U.S. Cl.

CPC ............... *A61K 8/25* (2013.01); *A61K 8/26* (2013.01); *A61Q 11/00* (2013.01)

(58) Field of Classification Search

CPC .. A61K 2800/651; A61K 8/0241; A61K 8/24; A61Q 11/00; C01B 25/32; C01P 2002/72; C01P 2002/74; C01P 2006/12

See application file for complete search history.

(56) References Cited

FOREIGN PATENT DOCUMENTS

| JP | S55-057514 A | 4/1980 |
|---|---|---|
| JP | S62-273907 A | 11/1987 |
| JP | H02-022214 A | 1/1990 |
| JP | H09-020508 A | 1/1997 |
| JP | H10-017449 A | 1/1998 |
| JP | 2002-179541 A | 6/2002 |
| JP | 2005-075722 A | 3/2005 |
| JP | 2005-325102 A | 11/2005 |
| JP | 2010-208896 A | 9/2010 |
| JP | 2010-222325 A | 10/2010 |
| JP | 2014-181231 A | 9/2014 |
| JP | 2017-036176 A | 2/2017 |
| JP | 2017-048162 A | 3/2017 |
| JP | 2018-104302 A | 7/2018 |
| WO | WO 2008/056453 A1 | 5/2008 |
| WO | WO-2011055709 A1 * | 5/2011 ............... A61K 8/33 |
| WO | WO 2013/117913 A2 | 8/2013 |
| WO | WO 2014/038195 A1 | 3/2014 |

OTHER PUBLICATIONS

Cacciotti et al., High thermally stable Mg-substituted tricalcium phosphate via precipitation, Ceramics International, 2011, pp. 127-137, Elsevier.

Seo et al., Effect of milling time on the viscosity of hydroxyapatite suspension, Current Applied Physics, Feb. 8, 2012, pp. 571-575, Elsevier.

A third party observation dated Apr. 22, 2021 filed against the corresponding International application No. PCT/JP2019/051625.

May 24, 2022, Japanese Office Action issued for corresponding JP Application No. 2019-121902.

May 24, 2022, Japanese Office Action issued for corresponding JP Application No. 2019-121905.

May 24, 2022, Japanese Office Action issued for corresponding JP Application No. 2019-121912.

May 31, 2022, Japanese Office Action issued for corresponding JP Application No. 2019-121916.

Sep. 26, 2022, European Search Report issued for related EP Application No. 19904702.8.

Color/Gloss: Color measurement, retrieved from https://www.cerij.or.jp/service/05_polymer/color_glossiness_01.html on Jul. 27, 2022, p. 1, Chemicals Evaluation and Research Institute, Japan (CERI).

A Story of Light and Color Part 1, #32 Color Difference and Uniform Color Space, pp. 1-6, retrieved from: https://www.ccs-inc.co.jp/guide/column/light_color/vol32.html, including copy obtained from Wayback Machine from Aug. 11, 2017.

\* cited by examiner

COMPOSITION FOR ORAL CAVITY

CROSS REFERENCE TO PRIOR APPLICATION

This application is a National Stage Patent Application of PCT International Patent Application No. PCT/JP2019/051625 (filed on Dec. 27, 2019) under 35 U.S.C. § 371, which claims priority to Japanese Patent Application Nos. 2018-245027 (filed on Dec. 27, 2018), 2019-121902 (filed on Jun. 28, 2019), 2019-121905 (filed on Jun. 28, 2019), 2019-121912 (filed on Jun. 28, 2019), and 2019-121916 (filed on Jun. 28, 2019), which are all hereby incorporated by reference in their entirety.

TECHNICAL FIELD

The present disclosure relates to an oral composition, and more specifically to an oral composition containing hydroxyapatite particles. The disclosures of the references (in particular, JP2017-036176A) cited in the present specification are incorporated herein by reference in their entirety.

BACKGROUND ART

Hypersensitivity in teeth develops when dentin of the teeth is exposed, for example, due to physical wear caused by brushing or chemical wear caused by acids. When the dentin is exposed, external stimuli impact nerves in the dentinal tubules in the dentin, making pain likely to occur.

Hypersensitivity has been addressed by sealing the dentinal tubules by using, for example, particles of fluoride or aluminum salts (e.g., PTL 1), to prevent external stimuli from reaching the nerves. However, many conventional methods are insufficient in terms of adhesion properties after sealing, and the persistence of the effect remains to be addressed.

CITATION LIST

Patent Literature

PTL 1: JP2010-222325A
PTL 2: JP2017-036176A

SUMMARY OF INVENTION

Technical Problem

The present inventors conducted research with the aim of providing a technique for reducing hypersensitivity in teeth.

Solution to Problem

The present inventors found that specific hydroxyapatite particles (hydroxyapatite particles with a ratio of the diffraction peak intensity around $2\theta=32°$ to the diffraction peak intensity around $2\theta=26°$ of 0.8 to 1.6 in an X-ray diffraction pattern) have properties to seal dentinal tubules and excellent adhesion properties in dentinal tubules. The inventors then found that the particles could reduce hypersensitivity in teeth, and conducted further research based on these findings.

The present disclosure includes, for example, the subject matter described in the following items.

Item 1.
An oral composition comprising hydroxyapatite particles, wherein the hydroxyapatite particles have a ratio of a diffraction peak intensity around $2\theta=32°$ to a diffraction peak intensity around $2\theta=26°$ of 0.8 to 1.6 in an x-ray powder diffraction pattern as measured with a CuKα characteristic X-ray.

Item 2.
The oral composition according to Item 1, wherein the hydroxyapatite particles have a Ca/P molar ratio of less than 1.67.

Item 3.
The oral composition according to Item 1 or 2, wherein the hydroxyapatite particles have a median diameter of 5 μm or less.

Item 4.
The oral composition according to any one of Items 1 to 3, wherein the hydroxyapatite particles have a specific surface area of 30 to 200 $m^2/g$.

Item 5.
The oral composition according to any one of Items 1 to 4, wherein the hydroxyapatite particles have a ratio of a diffraction peak intensity around $2\theta=34°$ to a diffraction peak intensity around $2\theta=32°$ of 1 or less in an x-ray powder diffraction pattern as measured with a CuKα characteristic X-ray.

Item 6.
The oral composition according to any one of Items 1 to 5, wherein the hydroxyapatite particles are each an aggregate of plate-like crystals of hydroxyapatite.

Item 7.
The oral composition according to any one of Items 1 to 6, further comprising a fluorine compound.

Item 8.
The oral composition according to any one of Items 1 to 6, further comprising tin fluoride.

Item 9.
The oral composition according to any one of Items 1 to 8, further comprising potassium nitrate.

Item 10.
The oral composition according to any one of Items 1 to 9, further comprising silica.

Item 11.
The oral composition according to any one of Items 1 to 10, further comprising aluminum lactate.

Item 12.
The oral composition according to any one of Items 1 to 11, which is for use in the prevention or improvement of hypersensitivity.

Item 13.
The oral composition according to any one of Items 1 to 12, wherein the hydroxyapatite particles are those produced by a method for producing a hydroxyapatite particle comprising mixing an aqueous alkaline phosphate solution with a pH of 4 or more and less than 7 with a calcium hydroxide slurry to react the mixture at 35 to 85° C.

Item 14.
The oral composition according to Item 13, wherein the calcium hydroxide slurry is a ground calcium hydroxide slurry.

Item 15.
The oral composition according to Item 13 or 14, wherein the calcium hydroxide slurry has a reactivity with oxalic acid of 40 minutes or less, the reactivity with oxalic acid being a period of time (minutes) until a pH of 7.0 is achieved after 40 g of an aqueous oxalic acid solution that is maintained at 25±1° C. and that has a concentration of 0.5 mol/L is added at one time to 50 g of the calcium hydroxide slurry that is adjusted to a concentration of 5 mass % and that is maintained at 25±1° C.

Item 16.
The oral composition according to any one of Items 13 to 15, wherein the calcium hydroxide slurry has a BET specific surface area of 5 m/g or more.
Item 17
The oral composition according to any one of Items 1 to 16, wherein the silica has a mean particle size of 2 to 20 µm.

Advantageous Effects of Invention

An oral composition containing novel hydroxyapatite particles is provided. The oral composition has properties to seal dentinal tubules and excellent adhesion properties in dentinal tubules.

Additionally, the use of the novel hydroxyapatite particles in combination with various components in an oral composition leads to various advantageous effects of the oral composition.

DESCRIPTION OF EMBODIMENTS

Figure 1:
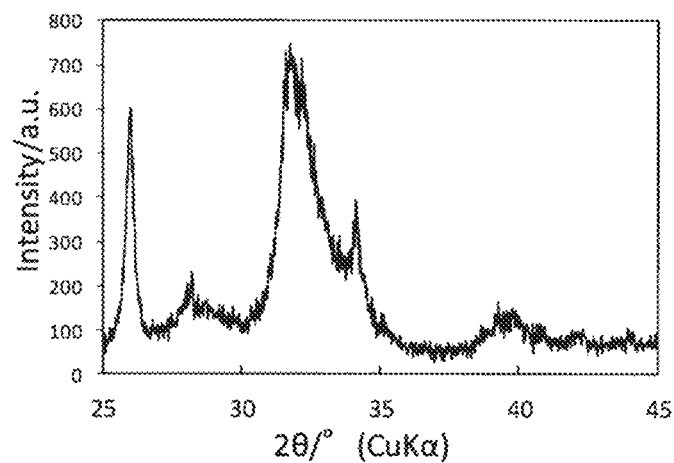
FIG. 1 shows the X-ray diffraction peaks of the hydroxyapatite particles in Example 1.

Embodiments encompassed in the present disclosure are described in more detail below. The present disclosure preferably encompasses oral compositions, in particular, oral compositions containing specific hydroxyapatite particles. However, the present disclosure is not limited to the compositions, and the present disclosure encompasses everything that is disclosed in the present specification and recognizable by those skilled in the art.

The oral compositions encompassed in the present disclosure contain specific hydroxyapatite particles. In the present specification, such an oral composition may be referred to as "the oral composition according to the present disclosure."

The specific hydroxyapatite particles have a ratio of the diffraction peak intensity around $2\theta=32°$ to the diffraction peak intensity around $2\theta=26°$ of 0.8 to 1.6 in an X-ray diffraction pattern. In the present specification, the hydroxyapatite particles may be referred to as "the particles according to the present disclosure."

The diffraction peak around $2\theta=26°$ is a peak of hydroxyapatite, specifically a diffraction peak at $2\theta=25.5$ to $26.5°$, and preferably a diffraction peak at $2\theta=25.8$ to $26.2°$. When there are multiple diffraction peaks around $2\theta=26°$, the diffraction peak around $2\theta=26°$ is the diffraction peak with the highest intensity.

The diffraction peak around $2\theta=32°$ is a peak of hydroxyapatite, specifically a diffraction peak at $2\theta=31.5$ to $32.5°$, and preferably a diffraction peak at $2\theta=31.8$ to $32.2°$. When there are multiple diffraction peaks around $2\theta=32°$, the diffraction peak around $2\theta=32°$ is the diffraction peak with the highest intensity.

In the present specification, the X-ray diffraction pattern is an x-ray powder diffraction pattern measured with CuKα characteristic X-rays. The measurement conditions are one of the following:

Measurement Condition 1
Target: Cu, tube voltage: 40 kV, tube current: 30 mA, sampling range: 0.02°, scanning rate: 2.00°/min, divergence slit: 1.00, scatter slit: 1.0°, light-receiving slit: 0.3 mm.

Measurement Condition 2
Target: Cu, tube voltage: 40 kV, tube current: 15 mA, sampling range: 0.02°, scanning rate: 2.00°/min, divergence slit: 1.25°, scatter slit: 1.25°, light-receiving slit: 0.3 mm.

The measurement device for use may be, for example, a MultiFlex 2 kW X-ray diffractometer (Rigaku Co., Ltd.) or a Miniflex 500 X-ray diffractometer (Rigaku Co., Ltd.). It is preferable to perform measurement with a MultiFlex 2 kW X-ray diffractometer under Measurement Condition 1 or to perform measurement with a Miniflex 500 X-ray diffractometer under Measurement Condition 2.

The particle according to the present disclosure has a ratio of the diffraction peak intensity around $2\theta=32°$ to the diffraction peak intensity around $2\theta=26°$ (32°/26°) of 0.8 to 1.6. The upper limit or the lower limit of the ratio of peak intensity may be, for example, 0.85, 0.9, 0.95, 1.0, 1.05, 1.1, 1.15, 1.2, 1.25, 1.3, 1.35, 1.4, 1.45, 1.5, or 1.55. For example, the ratio of peak intensity is preferably 0.8 to 1.5, more preferably 0.9 to 1.3, still more preferably 1.0 to 1.25, yet more preferably 1.05 to 1.2, and particularly preferably 1.05 to 1.15. The upper limit of the ratio of peak intensity may be 1.59 or 1.58.

The particles according to the present disclosure are each preferably an aggregate of plate-like crystals of hydroxyapatite. The plate-like crystals that constitute each particle according to the present disclosure may be of any shape; examples of the shape include a circle, a polygon (in particular, a hexagon), a rod-like shape, and combinations of these shapes. The plate-like crystals may be either in a state in which the plate-like crystals are folded at their plane or a state in which the plate-like crystals are not folded at their plane, with the planar structure maintained. Typically, plate-like hydroxyapatite crystals have a structure called a "hexagonal crystal," in which the top faces are c-planes and the side faces are a-planes. When the particle is formed of multiple crystals, each crystal is called "crystallite."

The particle according to the present disclosure contains hydroxyapatite as a major component, and is preferably a particle consisting essentially of hydroxyapatite. In an X-ray diffraction pattern of the particle according to the present disclosure, even though the peaks of other substances (e.g., monetite) are contained, such peaks are not separately observed, or the peak intensity of other substances is relatively low. Thus, the particle according to the present disclosure is distinguished from these particles whose peaks have a high peak intensity.

Not wishing to be bound by limited interpretation, it is speculated that partly due to the shape and structure shown in a specific X-ray diffraction pattern and the structure formed by aggregated plate-like particles, and the combination thereof, the particle according to the present disclosure exhibits excellent properties to seal dentinal tubules and excellent adhesion properties in dentinal tubules.

The particles according to the present disclosure preferably have a ratio of the diffraction peak intensity around $2\theta=34°$ to the diffraction peak intensity around $2\theta=32°$ of 1 or less in an X-ray diffraction pattern (34°/32°). The diffraction peak around $2\theta=34°$ is specifically a diffraction peak at $2\theta=33.5$ to 34.5°, and preferably a diffraction peak at $2\theta=33.8$ to 34.2°. When there are multiple diffraction peaks around $2\theta=34°$, the diffraction peak around $2\theta=34°$ refers to the diffraction peak with the highest intensity. The ratio of peak intensity is preferably 0.1 to 1, more preferably 0.2 to 0.9, still more preferably 0.3 to 0.8, yet more preferably 0.4 to 0.7, and particularly preferably 0.4 to 0.6.

In the particle according to the present disclosure, the sum of the areas of all of the diffraction peaks within $25.5°≤2\theta≤26.5°$ and the areas of all of the diffraction peaks within $31.5°≤2\theta≤32.5°$ is 30 to 45% based on the sum of the areas of all diffraction peaks within $25°≤2\theta≤35°$ taken as 100%. This value is preferably 33 to 42%, and more preferably 35 to 40%. In the particle according to the present disclosure, the crystallite size calculated from the diffraction peak of the (130) plane around $2\theta=40°$ is preferably 4 to 12 nm, and more preferably 5 to 10 nm. Not wishing to be bound by limited interpretation, it is speculated that the relatively low crystallinity facilitates the crystal growth in the dentinal tubules after the tubules are sealed, and thereby further improves the adhesion properties in the dentinal tubules.

The Ca/P molar ratio of the particles according to the present disclosure can be any value that hydroxyapatite can take. Not wishing to be bound by limited interpretation, some calcium is believed to be replaced with another element (e.g., sodium) in the particles according to the present disclosure. Thus, the Ca/P molar ratio can be a relatively low value. From this viewpoint, the Ca/P molar ratio of the particles according to the present disclosure is preferably less than 1.67, more preferably 1.65 or less or 1.60 or less, still more preferably 1.55 or less or 1.50 or less, and yet still more preferably 1.45 or less or 1.40 or less. The lower limit of the Ca/P molar ratio of the particles according to the present disclosure is not particularly limited, and may be, for example, 1.0, 1.1, or 1.2. The Ca/P molar ratio refers to a value determined by measuring the content of Ca and P in the particles according to the present disclosure by inductively coupled plasma optical emission spectroscopy and calculating the value from the measurement values.

The particles according to the present disclosure may have any median diameter (d50). From the standpoint of, for example, the properties to seal dentinal tubules and adhesion properties, the median diameter of the particles according to the present disclosure is preferably 5 μm or less, and more preferably 4.5 μm or less. The lower limit of the median diameter is not particularly limited, and can be, for example, 1 μm or more, 2 μm or more, or 3 μm or more. More specifically, the median diameter is, for example, 1 to 5 μm. The median diameter refers to a value measured by a laser diffraction-scattering technique. More specifically, the median diameter refers to a value measured by dry particle size distribution measurement with a laser diffraction particle size distribution analyzer.

The particles according to the present disclosure may have any specific surface area. From the standpoint of, for example, the properties to seal dentinal tubules and adhesion properties, the specific surface area of the particles according to the present disclosure is, for example, 30 $m^2/g$ or more, preferably 40 $m^2/g$ or more, more preferably 50 $m^2/g$ or more, and still more preferably 55 $m^2/g$ or more. The upper limit of the specific surface area is not particularly limited, and is, for example, 200 $m^2/g$, 170 $m^2/g$, 150 $m^2/g$, 120 $m^2/g$, 100 $m^2/g$, or 90 $m^2/g$. The specific surface area refers to a value measured by the nitrogen gas adsorption method.

The particles according to the present disclosure preferably react with saliva to exhibit improved crystallinity.

"Improved crystallinity" as used here means that sharpness of at least one peak (preferably 1, 2, 3, 4, or more peaks) is improved after the reaction with saliva as compared with that before the reaction with saliva (more specifically, the diffraction intensity is improved) in an x-ray powder diffraction pattern measured with CuKα characteristic X-rays. Saliva for use is artificial saliva ($CaCl_2$: 1.5 mM, $KH_2PO_4$: 0.9 mM, KCl: 130 mM, HEPES: 20 mM, pH 7.0 (KOH)). The reaction is performed by immersing the particles in saliva for 7 days.

The particles according to the present disclosure can be prepared, for example, by a method for producing a hydroxyapatite particle comprising mixing an aqueous alkaline phosphate solution with a pH of 4 or more and less than 7 with a calcium hydroxide slurry to react the mixture at 35 to 85° C.

The alkaline phosphate can be any alkaline phosphate, and includes hydrates and anhydrides. Examples of alkaline phosphates include sodium dihydrogen phosphate, disodium hydrogen phosphate, trisodium phosphate, tetrasodium pyrophosphate, potassium dihydrogen phosphate, dipotassium hydrogen phosphate, and tripotassium phosphate; the alkaline phosphate is preferably a sodium phosphate, such as sodium dihydrogen phosphate, disodium hydrogen phosphate, and trisodium phosphate, and more preferably sodium dihydrogen phosphate.

The concentration of the alkaline phosphate in the aqueous alkaline phosphate solution is not particularly limited, and is, for example 3 to 50 mass %. The concentration of the alkaline phosphate is preferably 3 to 30 mass %, more preferably 5 to 20 mass %, and still more preferably 7 to 15 mass %.

The pH of the aqueous alkaline phosphate solution is preferably 4 or more and less than 7. The pH of the aqueous alkaline phosphate solution is more preferably 5 to 6.5. As described later, when the aqueous alkaline phosphate solution has a relatively low pH (e.g., a pH of 4 or more and less than 5), it is preferred that an anhydride be used as an alkaline phosphate, and that the reaction temperature be set to a relatively high temperature, for example, 65 to 85° C., preferably 70 to 85° C., and more preferably 75 to 85° C.

The calcium hydroxide slurry is reactive with oxalic acid. The calcium hydroxide slurry is preferably a slurry of calcium hydroxide that has specific reactivity with oxalic acid.

The reactivity with oxalic acid is expressed, for example, by the following definition.
Reactivity with Oxalic Acid: a period of time (minutes) until a pH of 7.0 is achieved after 40 g of an aqueous oxalic acid solution that is maintained at 25±1° C. and that has a concentration of 0.5 mol/L is added at one time to 50 g of a calcium hydroxide slurry that is adjusted to a concentration of 5 mass %, and that is maintained at 25±1° C.

The specific reactivity with oxalic acid expressed by the above definition is preferably 1 to 40 minutes, more preferably 5 to 30 minutes, and still more preferably 10 to 20 minutes.

The calcium hydroxide slurry has a BET specific surface area of preferably 5 $m^2/g$ or more, and more preferably 6 $m^2/g$ or more. The upper limit of the BET specific surface area is not particularly limited, and is, for example, 20 $m^2/g$, 15 $m^2/g$, or 10 $m^2/g$.

A calcium hydroxide slurry with a high reactivity with oxalic acid, having the specific reactivity with oxalic acid described above) can be typically obtained by grinding a calcium hydroxide slurry. Grinding can further increase the reactivity with oxalic acid (the period of time defined above is further shortened). Grinding is performed by using, for example, a bead mill. The conditions for grinding are not particularly limited. For example, the conditions according to the method disclosed in JP2017-036176A can be used.

The calcium hydroxide slurry is prepared, for example, by reacting quicklime (calcium oxide) obtained by calcining limestone with water. For example, a calcium hydroxide slurry can be obtained by calcining limestone in a kiln at about 1000° C. to form quicklime, pouring in hot water in an amount about 10 times that of the quicklime, and stirring the mixture for 30 minutes.

The solids concentration of the calcium hydroxide slurry is not particularly limited, and is, for example, 1 to 30 mass %, preferably 3 to 20 mass %, more preferably 5 to 15 mass %, and still more preferably 6 to 12 mass %.

The amount ratio of the calcium hydroxide slurry to the aqueous alkaline phosphate solution is not particularly limited as long as hydroxyapatite particles can be produced. The amount ratio is preferably adjusted such that the Ca/P molar ratio results in preferably 0.3 to 0.7, more preferably 0.4 to 0.6, and still more preferably 0.45 to 0.55.

The mode in which the aqueous alkaline phosphate solution is mixed with the calcium hydroxide slurry is not particularly limited. Examples include a mode in which the calcium hydroxide slurry is added to a reaction vessel containing the aqueous alkaline phosphate solution (mode 1), a mode in which the aqueous alkaline phosphate solution is added to a reaction vessel containing the calcium hydroxide slurry (mode 2), and a mode in which the aqueous alkaline phosphate solution and the calcium hydroxide slurry are added to a reaction vessel simultaneously (mode 3). Of these, mode 1 is preferable. When the aqueous alkaline phosphate solution and/or the calcium hydroxide slurry is added to a reaction vessel, the liquid in the reaction vessel is typically stirred.

The addition of the aqueous alkaline phosphate solution and/or the calcium hydroxide slurry to a reaction vessel is preferably performed for a predetermined period of time. The period of time from the start of addition until the end of addition is, for example, 10 to 90 minutes, preferably 20 to 60 minutes, and more preferably 20 to 40 minutes.

The reaction is typically performed with stirring. The reaction temperature is 35 to 85° C. The reaction temperature is preferably 40 to 75° C., more preferably 45 to 70° C., still more preferably 50 to 70° C., and yet more preferably 55 to 65° C. When the aqueous alkaline phosphate solution has a relatively low pH (e.g., a pH of 4 or more and less than 5), the reaction temperature is a relatively high temperature, for example, 65 to 85° C., preferably 70 to 85° C., and more preferably 75 to 85° C. The reaction time (a time period that starts after the aqueous alkaline phosphate solution and the calcium hydroxide slurry have been fully mixed; in modes 1 to 3, a time period that starts after the addition of the aqueous alkaline phosphate solution and the calcium hydroxide slurry is ended) is, for example, 10 to 180 minutes, preferably 20 to 120 minutes, more preferably 40 to 90 minutes, and still more preferably 50 to 70 minutes.

With no particular limitation, it is preferable to be attentive to the pH of the aqueous alkaline phosphate solution before mixing it with the calcium hydroxide slurry and whether the alkaline phosphate is a hydrate or a nonhydrate when producing the particles according to the present disclosure. For example, when the alkaline phosphate for use is an anhydride, it is preferable to set the pH of the aqueous alkaline phosphate solution for use to a relatively low pH (e.g., a pH of 4 or more and less than 5, preferably 4 or more and 4.5 or less). For example, when the alkaline phosphate for use is a hydrate, it is preferable to set the pH of the aqueous alkaline phosphate solution for use to a relatively high pH (e.g., a pH of 5 or more and 6.5 or less). Additionally, it is preferable to add the calcium hydroxide slurry to the aqueous alkaline phosphate solution and mix them, rather than to add the aqueous alkaline phosphate solution to the calcium hydroxide slurry and mix them. Additionally, the calcium hydroxide slurry for use preferably has a reactivity with oxalic acid of about 5 to 30 minutes. The particles that have the properties described above according to the present disclosure can be preferably obtained by producing the particles while paying attention to these conditions.

The particles according to the present disclosure formed by performing the above step can be optionally subjected to purification. Examples of purification include filtration and washing with water. The particles according to the present disclosure can also optionally be subjected to drying.

The particles according to the present disclosure have properties to seal dentinal tubules and excellent adhesion properties in dentinal tubules. Thus, an oral composition containing the particles according to the present disclosure (i.e., the oral composition according to the present disclosure) can be preferably used particularly in the prevention or improvement of hypersensitivity.

The particles according to the present disclosure may be present in an oral composition, for example, in an amount of about 0.1 to 10 mass %. The upper limit or the lower limit of the amount may be, for example, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, or 9.5 mass %. For example, the range of amount may be 0.2 to 9.5 mass %, 0.5 to 9 mass %, or 1 to 8 mass %.

The oral composition according to the present disclosure can be produced by an ordinary method and can be used in, for example, pharmaceutical products, quasi-pharmaceutical products, and cosmetics. Although the form of the oral composition according to the present disclosure is not particularly limited, the oral composition can be made into a form (dosage form), such as an ointment, a paste, a dermatological paste, a gel, a liquid, a spray, a mouthwash, a liquid dentifrice, a toothpaste, or a liniment in accordance with an ordinary method. Of these, a mouthwash, a liquid dentifrice, a toothpaste, paste, a liquid, a spray, a gel, and a liniment are preferable, and a toothpaste, a paste, and a gel are more preferable. It is also preferable to perform brushing with the oral composition on a toothbrush, or after the oral composition is applied into the mouth. Thus, the oral composition is preferably in the form suitable for brushing. Brushing can push the particles according to the present disclosure into to the cavities of the tooth dentin, thus providing the effects more effectively.

In addition to the particles according to the present disclosure, the oral composition according to the present disclosure may further contain one or a combination of two or more optional components that can be formulated into oral compositions to the extent that the effects are not impaired.

Examples of such components include silica. In other words, the oral composition according to the present disclosure preferably contains the particles according to the present disclosure and silica. Silica is preferably silica particles.

Unlike the conventional hydroxyapatite particles, the particles according to the present disclosure can provide the effect of greatly preventing an oral composition from dripping off a toothbrush when the particles according to the present disclosure are contained in combination with silica in the oral composition. This also greatly improves the usability of the oral composition and is thus preferable.

The silica can be any silica as long as the above effects are brought about in the oral composition according to the present disclosure. Any silica known in the art is usable. For example, precipitated silica is usable. Polishing silica and/or thickening silica is also usable. Additionally, silica such as fumed silica and molten silica is also usable. Although there is no particular limitation, the silica preferably has a mean particle size of 2 to 20 µm. The mean particle size refers to a value measured by a laser diffraction-scattering technique. The silica preferably has a pH (5 aq. sol.) of, for example, about 5.5 to 7.5 or about 6 to 7. The pH (5 aq. sol.) refers to a pH at a point when 5 g of silica is dispersed in 95 mL of purified water. The silica can be contained in an amount of, for example, about 1 to 30 mass % in the oral composition. The upper limit or the lower limit of the amount may be, for example, 2, 3, 4, 5, 6, 7, 8, 9, 10, 11, 12, 13, 14, 15, 16, 17, 18, 19, 20, 21, 22, 23, 24, 25, 26, 27, 28, or 29 mass %. For example, the range of amount is more preferably 2 to 25 mass % or 3 to 20 mass %.

The oral composition containing the particles according to the present disclosure and silica is preferred because such an oral composition can provide improved usability due to suppressed dropping-off of the composition from a toothbrush as well as reduced tooth hypersensitivity. Additionally, the oral composition is also advantageous in that the oral composition is unlikely to undergo water release and favorably maintains its color (white) when stored at high temperatures (e.g., 55° C.) for a long period of time (e.g., 4 months).

Another preferable example of components to be added to the oral composition is aluminum lactate.

Because aluminum lactate is a medicinal ingredient for preventing hypersensitivity, it is preferable to add aluminum lactate to the oral composition according to the present disclosure for this effect. However, oral compositions containing aluminum lactate often turn yellow (yellowing). This deteriorates the appearance of the oral composition and causes demanders (consumers) to avoid using the composition. Thus, it is desirable to suppress this yellowing. It is preferable for the oral composition to contain the particles according to the present disclosure in addition to aluminum lactate because the yellowing of the oral composition is efficiently suppressed. Thus, the oral composition according to the present disclosure preferably encompasses oral compositions in which the yellowing caused by aluminum lactate is suppressed by the particles according to the present disclosure. The particles according to the present disclosure can also be considered suitably usable in suppressing the yellowing of oral compositions caused by aluminum lactate.

Aluminum lactate can be present in an amount of, for example, about 1 to 3 masse, and more preferably about 1 to 2.5 mass % in the oral composition.

Although there is no particular limitation, the mass ratio of the aluminum lactate to the particles according to the present disclosure contained in the oral composition is preferably about 0.05 to 5 (the ratio of aluminum lactate to the particles according to the present disclosure taken as 1). The upper limit or the lower limit of the range may be 0.1, 0.2, 0.3, 0.4, 0.5, 0.6, 0.7, 0.8, 0.9, 1, 1.5, 2, 2.5, 3, 3.5, 4, or 4.5. For example, the range of the mass ratio may be about 0.2 to 4 or 0.5 to 3.

Potassium nitrate, like aluminum lactate, is also a medicinal ingredient for preventing hypersensitivity. Thus, it is preferable to add potassium nitrate to the oral composition according to the present disclosure for the effect.

Another preferable example of components to be added to the oral composition is a fluorine compound.

Unlike conventional hydroxyapatite particles, the particles according to the present disclosure can provide the effect of greatly preventing an oral composition from turning yellow (i.e., yellowing) when the particles according to the present disclosure are contained in combination with a fluorine compound in the oral composition. It is preferable to suppress yellowing because yellowing can be a reason for consumers to avoid selecting oral compositions.

The fluorine compound for preferable use can be, for example, a fluorine compound known in the field of oral compositions. More specifically, the fluorine compound for use includes, for example, sodium monofluorophosphate, sodium fluoride, and tin fluoride, with sodium monofluorophosphate and sodium fluoride being more preferable.

For example, the fluorine compound is present in an amount of preferably 2000 ppm or less, and more preferably 50 to 2000 ppm in the oral composition on a fluoride-ion concentration basis. The upper limit or the lower limit may be, for example, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, or 1950 ppm. For example, the range is more preferably 100 to 1800 ppm or 200 to 1600 ppm.

Unlike conventional hydroxyapatite particles, the particles according to the present disclosure can provide the effect of greatly enhancing shape retention (in particular, stability over time) and preventing the oral composition from dropping off a toothbrush when the particles according to the present disclosure are contained in combination with tin fluoride in the oral composition. This also greatly improves the usability of the oral composition and is thus preferable. Thus, among fluorine compounds, tin fluoride not only provides a yellowing suppression effect but also contributes to improving usability when contained in the oral composition. For example, tin fluoride is preferably stannous fluoride ($SnF_2$).

For example, tin fluoride is present in an amount of preferably 1 mass % or less, and more preferably 0.01 to 1 mass %, in the oral composition. The upper limit or the lower limit may be, for example, 0.95, 0.9, 0.85, 0.8, 0.75, 0.7, 0.65, 0.6, 0.55, 0.5, 0.45, 0.4, 0.35, 0.3, 0.25, 0.2, 0.15, 0.1, or 0.05 mass %. For example, the range may be 0.01 to 0.75 mass % or 0.05 to 0.5 mass %.

Tin fluoride can be preferably present in the amount within the ranges described above on a fluoride-ion concentration basis in the oral composition in either case: when tin fluoride alone is used as a fluorine compound, and when tin fluoride is used in combination with other fluorine compounds (e.g., sodium monofluorophosphate and/or sodium fluoride).

The present inventors found that oral compositions containing potassium nitrate in addition to known hydroxyapatite particles and a fluorine compound exhibit low stability of contained fluorine. The inventors also found that the use of the particles according to the present disclosure as hydroxyapatite particles in an oral composition containing a fluorine compound and potassium nitrate can suppress the decrease in stability of fluorine. Thus, the present disclosure also preferably encompasses oral compositions containing the particles according to the present disclosure, potassium nitrate, and a fluorine compound.

The amount of potassium nitrate added to an oral composition is preferably within a range in which the effects can be brought about, and is not particularly limited. The amount of potassium nitrate is, for example, about 1 to 10 mass %, about 2 to 8 mass %, or about 3 to 7 mass %.

Examples of other optional components to be added include surfactants, such as nonionic surfactants, anionic surfactants, and ampholytic surfactants. Specific examples of nonionic surfactants include sugar fatty acid esters, such as sucrose fatty acid esters, maltose fatty acid esters, and lactose fatty acid esters; fatty acid alkanolamides; sorbitan fatty acid esters; fatty acid monoglyceride; polyoxyethylene alkyl ethers with a polyoxyethylene addition factor of 8 to 10, and 13 to 15 carbon atoms in the alkyl group; polyoxyethylene alkyl phenyl ethers with a polyoxyethylene addition factor of 10 to 18, and 9 carbon atoms in the alkyl group; diethyl sebacate; polyoxyethylene hydrogenated castor oil; and fatty acid polyoxyethylene sorbitan. Examples of anionic surfactants include sulfates, such as sodium lauryl sulfate and sodium polyoxyethylene lauryl ether sulfate; sulfosuccinates, such as sodium lauryl sulfosuccinate and sodium polyoxyethylene lauryl ether sulfosuccinate; acyl amino acid salts, such as sodium cocoyl sarcosine and sodium lauroyl methylalanine; and sodium cocoyl methyl taurine. Examples of ampholytic surfactants include betaine acetate activators, such as betaine lauryl dimethylamino acetate and coconut oil fatty acid amide propyldimethylamino acetate betaine; imidazoline activators, such as sodium N-cocoyl-N-carboxymethyl-N-hydroxyethylethylenediamine; and amino acid activators, such as N-lauryl diaminoethyl glycine. These surfactants can be added singly or in a combination of two or more. The amount of the surfactant added is typically 0.1 to 5 mass % based on the total amount of the composition.

Additionally, a sweetener, such as saccharin sodium, acesulfame potassium, stevioside, neohesperidin dihydrochalcone, perillatin, thaumatin, aspartylphenylalanine methyl ester, and p-methoxycinnamic aldehyde, can be added. These sweeteners can be used singly or in a combination of two or more. The sweetener can be added in an amount of 0.01 to 1 mass % based on the total amount of the composition.

The binder for use can be, for example, one, or a combination of two or more, of the following binders: cellulose derivatives, such as sodium carboxymethyl cellulose, carboxy methyl ethyl cellulose salts, hydroxyethyl cellulose, hydroxypropyl cellulose, and hydroxypropyl methylcellulose; microbial polymers, such as xanthan gum and gellan gum; natural polymers or natural rubber, such as gum tragacanth, gum karaya, gum arabic, carrageenan, and dextrin; synthetic polymers, such as polyvinyl alcohol and polyvinyl pyrrolidone; inorganic binders, such as Veegum; and cationic binders, such as O-[2-hydroxy-3-(trimethylammonio)propyl]hydroxyethyl cellulose chloride.

Additionally, wetting agents such as the following can be added singly or in a combination of two or more: sorbitol, glycerol, polypropylene glycol, xylit, maltit, lactit, and polyoxyethylene glycol.

Preservatives such as the following can be added singly or in a combination of two or more: parabens, such as methylparaben, ethylparaben, propylparaben, and butylparaben, sodium benzoate, phenoxyethanol, and alkyldiaminoethylglycine hydrochloride.

Colorants such as the following can be added singly or in a combination of two or more: legally permitted pigments such as blue No. 1, yellow No. 4, red No. 202, and green No. 3; mineral-based pigments such as ultramarine, enhanced ultramarine, and ferric hexacyanoferrate; and titanium oxide.

pH Adjusters, such as the following can be added: citric acid, phosphoric acid, malic acid, pyrophosphoric acid, lactic acid, tartaric acid, glycerophosphoric acid, acetic acid, nitric acid, chemically possible salts thereof, and sodium hydroxide. These pH adjusters can be added singly or in a combination of two or more such that the composition has a pH of 4 to 8, and preferably 5 to 7. The amount of the pH adjuster is, for example, 0.01 to 2 wt %.

As a medicinal ingredient, a disinfectant may be added. Examples include cationic disinfectants, such as cetylpyridinium chloride, benzalkonium chloride, benzethonium chloride, chlorhexidine hydrochloride, and chlorhexidine gluconate; ampholytic disinfectants, such as dodecyl diaminoethylglycine; nonionic disinfectants, such as triclosan, and isopropyl methylphenol; and hinokitiol. Additionally, medicinal ingredients other than disinfectants can be added. For example, vitamin E, such as dl-α-tocopherol acetate, tocopherol succinate, or tocopherol nicotinate may be added in addition to the above fluoride such as sodium fluoride, sodium monofluorophosphate, and tin fluoride, aluminum lactate, and potassium nitrate. These medicinal ingredients cane be added singly or in a combination of two or more.

The following can also be added as a base singly or in a combination of two or more: for example, alcohol, silicon, apatite, white Vaseline, paraffin, liquid paraffin, microcrystalline wax, squalane, and Plastibase.

The optional components above are simply examples and are not intended to limit the optional components for use.

In the present specification, the term "comprising" includes consisting essentially of and consisting of. The present disclosure encompasses any combination of the elements described in the present specification.

The various characteristics (e.g., properties, structures, functions) described in each embodiment of the present disclosure can be combined in any way in specifying the subject matter encompassed in the present disclosure. Specifically, the present disclosure encompasses all subject matter formed by any possible combination of the characteristics described in the present specification.

EXAMPLES

The subject matter of the present disclosure is described in more detail below based in Examples. However, the subject matter of the present disclosure is not limited the Examples.

Example 1

A 10.7 mass % aqueous solution of sodium dihydrogen phosphate-2 hydrate and a ground calcium hydroxide slurry with a solids concentration of 8.6 mass % (BET specific surface area: 6.7 m$^2$/g, reactivity with oxalic acid: 15 minutes and 30 seconds, JP2017-036176A) were prepared so as to give a Ca/P molar ratio of 0.5. The aqueous solution of sodium dihydrogen phosphate-2 hydrate was placed in a stainless-steel beaker and heated to 60° C. with stirring. This temperature was maintained until the end of stirring. A 10% aqueous solution of NaOH was added to adjust the pH to 5.5. The calcium hydroxide slurry was added thereto for a period of 30 minutes. After completion of the addition, the mixture was further stirred for 1 hour, and then filtered and washed with water, followed by drying at 80° C., thereby obtaining hydroxyapatite particles (powder).

The obtained hydroxyapatite particles were measured for X-ray crystal diffraction, specific surface area, particle size distribution, and Ca/P molar ratio, and observed for shape.

Figure 2:
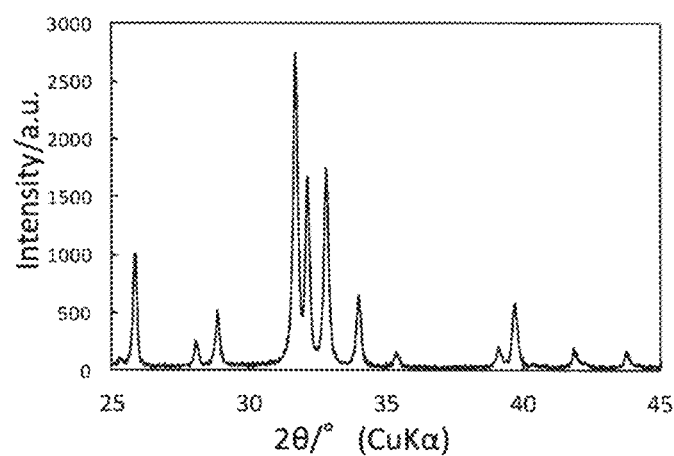
FIG. 2 shows the X-ray diffraction peaks of hydroxyapatite particles of a commercially available reagent.

Measurement was performed with a MultiFlex 2-kW X-ray diffractometer (produced by Rigaku Corporation) within the range of 2θ=25 to 45°. Measurement conditions: target: Cu; tube voltage: 40 kV; tube current: 30 mA; sampling range: 0.02°; scanning rate: 2.00°/min; divergence slit: 1.0°; scatter slit: 1.0°; light-receiving slit: 0.3 mm. FIG. 1 shows the results. FIG. 2 shows the X-ray diffraction pattern of hydroxyapatite, which is a commercially available reagent (reagent HAp). The ratio of the diffraction peak intensity of the (211) plane around 2θ=32° to the diffraction peak intensity of the (002) plane around 2θ=26° was 1.1, which was clearly lower than the peak intensity ratio 2.7 of the reagent HAp. This indicated that the obtained hydroxyapatite particles are aggregates of plate-like crystals with a relatively large part of the c-plane exposed. The sum of the areas of all of the diffraction peaks within the range of 25.5°≤2θ≤26.5° and the areas of all of the diffraction peaks within the range of 31.5°≤2θ≤32.5° was 37.2%, based on the sum of the areas of all of the diffraction peaks within the range of 25°≤2θ≤35° taken as 100%. This value is clearly lower than the 52.1% indicated by the reagent HAp; the relatively broad X-ray diffraction pattern also suggests low crystallinity. Additionally, the crystallite size calculated from the diffraction peak of the (130) plane around 2θ=40° was 7 nm, which is clearly smaller than the 52 nm indicated by the reagent HAp. This also suggests low crystallinity.

The specific surface area of the hydroxyapatite particles was measured by the nitrogen gas adsorption method with a fully automatic specific surface area analyzer (Macsorb HM model-1208, produced by Mountech Co. Ltd.). The specific surface area was 61.9 m$^2$/g.

The particle size distribution of the hydroxyapatite particles was measured in accordance with dry particle size distribution measurement with a laser diffraction particle size distribution analyzer (Mastersizer 3000). The median diameter (d50) was 3.76 μm.

The Ca/P molar ratio of the hydroxyapatite particles was determined by measuring the content of Ca and P with an iCAP6000 ICP-OES (produced by Thermo Fisher Scientific) by inductively coupled plasma optical emission spectroscopy, and calculating the ratio from the measurement values. The Ca/P molar ratio was 1.33.

Figure 3:
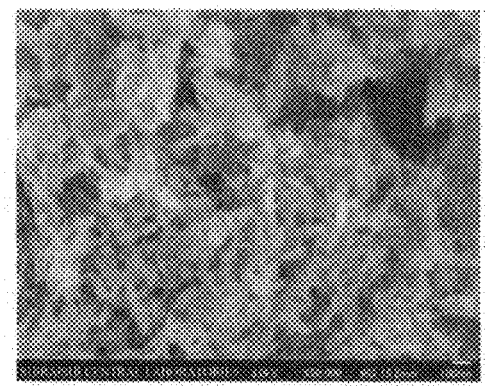
FIG. 3 shows an SEM photograph of the hydroxyapatite particles in Example 1.

The shape of the hydroxyapatite particles was observed with a scanning electron microscope (produced by JEOL Ltd., "SEM" below). FIG. 3 shows the results. The results indicated that the obtained hydroxyapatite particles were each an aggregate of plate-like crystals.

Example 2

A 10.7 mass % aqueous solution of sodium dihydrogen phosphate-2 hydrate and a ground calcium hydroxide slurry with a solids concentration of 8.6 mass % (BET specific surface area: 7.9 m$^2$/g, reactivity with oxalic acid: 12 minutes and 30 seconds, JP2017-036176A) were prepared so as to give a Ca/P molar ratio of 0.5. The aqueous solution of sodium dihydrogen phosphate-2 hydrate was placed in a stainless-steel beaker and heated to 60° C. with stirring. This temperature was maintained until the end of stirring. A 10% aqueous solution of NaOH was added to adjust the pH to 6.0. The calcium hydroxide slurry was added thereto for a period of 30 minutes. After completion of the addition, the mixture was further stirred for 1 hour, and then filtered and washed with water, followed by drying at 80° C., thereby obtaining hydroxyapatite particles (powder).

The obtained hydroxyapatite particles were measured for X-ray crystal diffraction and specific surface area, and observed for shape in the same manner as in Example 1.

Figure 4:
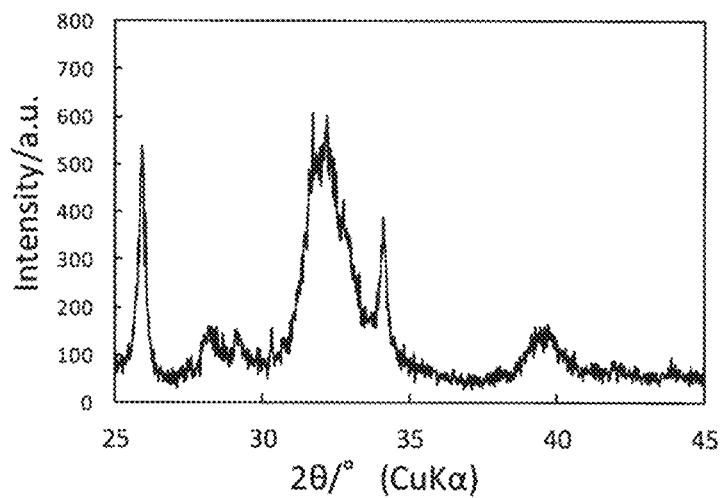
FIG. 4 shows the X-ray diffraction peaks of the hydroxyapatite particles in Example 2.

FIG. 4 shows the results of X-ray crystal diffraction. The ratio of the diffraction peak intensity of the (211) plane around 2θ=32° to the diffraction peak intensity of the (002) plane around 2θ=26° was 1.1, which was the same value as that of Example 1. The sum of the areas of all of the diffraction peaks within the range of 25.5°≤2θ≤26.5° and the areas of all of the diffraction peaks within the range of 31.5°≤2θ≤32.5° was 38.6% based on the sum of the areas of all of the diffraction peaks within the range of 25°≤2θ≤35° taken as 100%. The crystallite size calculated from the diffraction peak of the (130) plane around 2θ=40° was 7 nm.

The specific surface area was 75.4 m²/g.

Figure 5:
FIG. 5 shows an SEM photograph of the hydroxyapatite particles in Example 2.

FIG. 5 shows the results of shape observation. The results indicated that the obtained hydroxyapatite was in the form of aggregates of plate-like crystals, as in Example 1.

Example 3

A 10.7 mass %, aqueous solution of sodium dihydrogen phosphate-2 hydrate and a ground calcium hydroxide slurry with a solids concentration of 8.6 mass (BET specific surface area: 7.9 m²/g, reactivity with oxalic acid: 12 minutes and 30 seconds, JP2017-036176A) were prepared so as to give a Ca/P molar ratio of 0.5. The aqueous solution of sodium dihydrogen phosphate-2 hydrate was placed in a stainless-steel beaker and heated to 40° C. with stirring. This temperature was maintained until the end of stirring. A 10% aqueous solution of NaOH was added to adjust the pH to 5.5. The calcium hydroxide slurry was added thereto for a period of 50 minutes. After completion of the addition, the mixture was further stirred for 1 hour, and then filtered and washed with water, followed by drying at 80° C., thereby obtaining hydroxyapatite particles (powder).

The obtained hydroxyapatite particles were measured for X-ray crystal diffraction and specific surface area, and observed for shape in the same manner as in Example 1.

Figure 6:
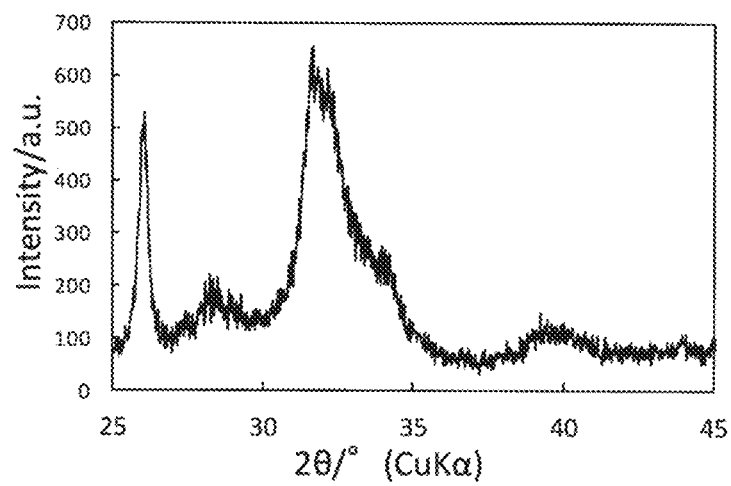
FIG. 6 shows the X-ray diffraction peaks of the hydroxyapatite particles in Example 3.

FIG. 6 shows the results of X-ray crystal diffraction. The ratio of the diffraction peak intensity of the (211) plane around 2θ=32° to the diffraction peak intensity of the (002) plane around 2θ=26° was 1.2, which was a value equivalent to that of Example 1. The sum of the areas of all of the diffraction peaks within the range of 25.5°≤2θ≤26.5° and the areas of all of the diffraction peaks within the range of 31.5°≤2θ≤32.5° was 36.0% based on the sum of the areas of all of the diffraction peaks within the range of 25°≤2θ≤35° taken as 100%. The crystallite size calculated from the diffraction peak of the (130) plane around 2θ=40° was 6 nm.

The specific surface area was 81.5 m²/g.

Figure 7:
FIG. 7 shows an SEM photograph of the hydroxyapatite particles in Example 3.

FIG. 7 shows the results of shape observation. The results indicated that the obtained hydroxyapatite particles were each an aggregate of plate-like crystals, as in Example 1.

Example 4

A 10.7 mass % aqueous solution of anhydrous sodium dihydrogen phosphate and a ground calcium hydroxide slurry with a solids concentration of 8.6 mass % (BET specific surface area: 7.9 m²/g, reactivity with oxalic acid: 12 minutes and 30 seconds, JP2017-036176A) were prepared so as to give a Ca/P molar ratio of 0.5. The aqueous solution of anhydrous sodium dihydrogen phosphate was placed in a stainless-steel beaker and heated to 80° C. with stirring. The pH was left at 4.2 and not adjusted. The calcium hydroxide slurry was added thereto for a period of 30 minutes. After completion of the addition, the mixture was further stirred for 1 hour, and then filtered and washed with water, followed by drying at 80° C., thereby obtaining hydroxyapatite particles (powder).

The obtained hydroxyapatite particles were measured for X-ray crystal diffraction and specific surface area, and observed for shape in the same manner as in Example 1.

Figure 8:
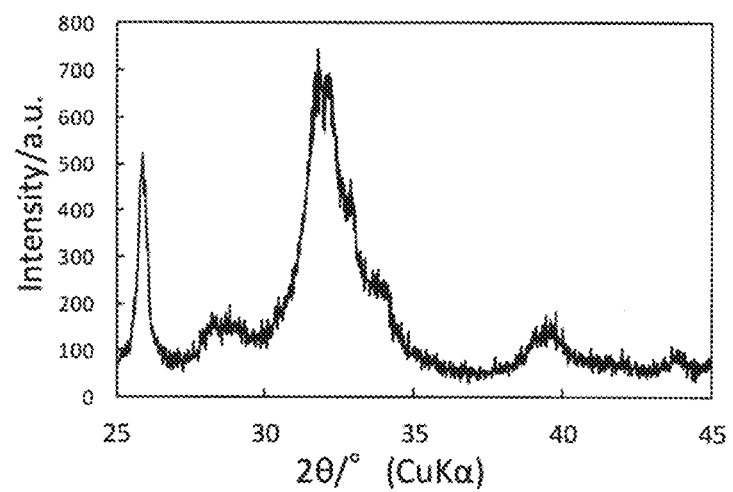
FIG. 8 shows the X-ray diffraction peaks of the hydroxyapatite particles in Example 4.

FIG. 8 shows the results of X-ray crystal diffraction. The ratio of the diffraction peak intensity of the (211) plane around 2θ=32° to the diffraction peak intensity of the (002) plane around 2θ=26° was 1.4, which was a value equivalent to that of Example 1. The sum of the areas of all of the diffraction peaks within the range of 25.5°≤2θ≤26.5° and the areas of all of the diffraction peaks within the range of 31.5°≤2θ≤32.5° was 37.8% based on the sum of the areas of all of the diffraction peaks within the range of 25°≤2θ≤35° taken as 100%. The crystallite size calculated from the diffraction peak of the (130) plane around 2θ=40° was 9 nm.

The specific surface area was 163.4 m²/g.

Figure 9:
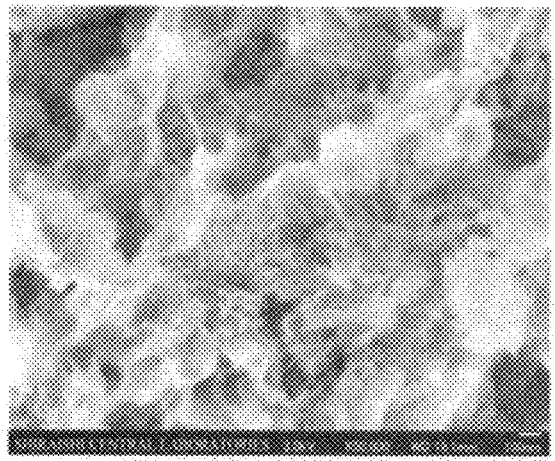
FIG. 9 shows an SEM photograph of the hydroxyapatite particles in Example 4.

FIG. 9 shows the results of shape observation. The results indicated that the obtained hydroxyapatite particles were each an aggregate of plate-like crystals, as in Example 1.

Example 5

A 10.7 mass % aqueous solution of anhydrous sodium dihydrogen phosphate and a ground calcium hydroxide slurry with a solids concentration of 8.6 mass % (BET specific surface area: 7.9 m²/g, reactivity with oxalic acid: 12 minutes and 30 seconds, JP2017-036176A) were prepared so as to give a Ca/P molar ratio of 0.5. The aqueous solution of anhydrous sodium dihydrogen phosphate was placed in a stainless-steel beaker and heated to 60° C. with stirring. The pH was left at 4.2 and not adjusted. The calcium hydroxide slurry was added thereto for a period of 30 minutes. After completion of the addition, the mixture was further stirred for 1 hour, and then filtered and washed with water, followed by drying at 80° C., thereby obtaining fine hydroxyapatite particles (powder).

The obtained fine hydroxyapatite particles were measured for X-ray crystal diffraction and specific surface area, and observed for shape in the same manner as in Example 1.

Figure 10A:
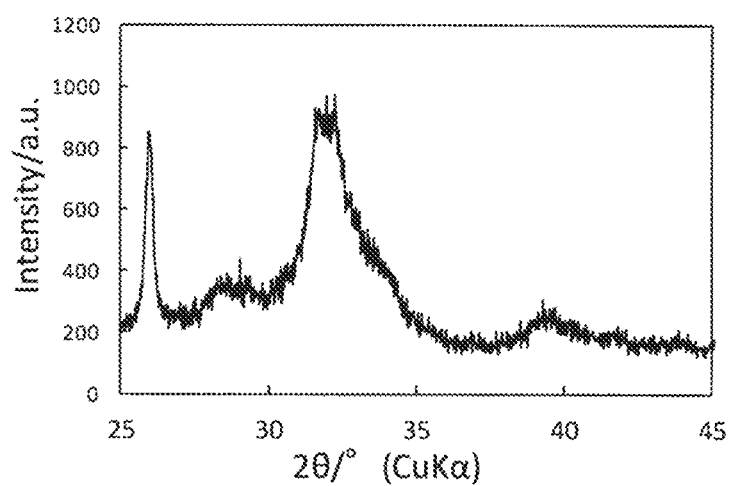
FIG. 10a shows the X-ray diffraction peaks of the fine hydroxyapatite particles in Example 5.

FIG. 10a shows the results of X-ray crystal diffraction. The ratio of the diffraction peak intensity of the (211) plane around 2θ=32° to the diffraction peak intensity of the (002) plane around 2θ=26° was 1.1, which was the same as that of Example 1. The sum of the areas of all of the diffraction peaks within the range of 25.5°≤2θ≤26.5° and the areas of all of the diffraction peaks within the range of 31.5°≤2θ≤32.5° was 31.6%, based on the sum of the areas of all of the diffraction peaks within the range of 25°≤2θ≤35° taken as 100%. The crystallite size calculated from the diffraction peak of the (130) plane around 2θ=40° was 7 nm.

The specific surface area was 94.7 m/g.

Figure 10B:
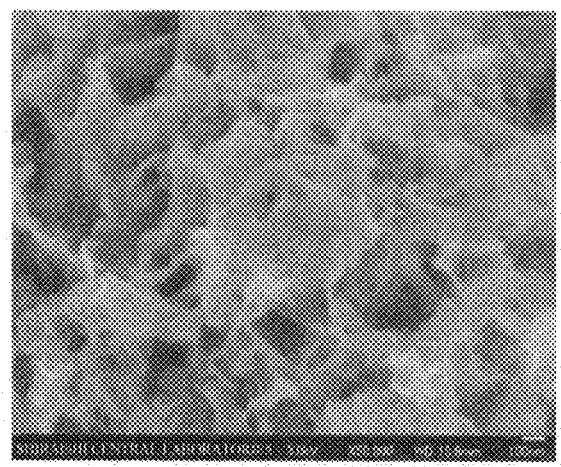
FIG. 10b shows an SEM photograph of the fine hydroxyapatite particles in Example 5.

FIG. 10b shows the results of shape observation. The results indicated that the obtained hydroxyapatite was in the form of aggregates of plate-like fine particles, as in Example 1.

Example 6

A 10.7 mass %, aqueous solution of anhydrous sodium dihydrogen phosphate and a ground calcium hydroxide slurry with a solids concentration of 8.6 mass % (BET specific surface area: 7.9 m²/g, reactivity with oxalic acid: 12 minutes and 30 seconds, JP2017-036176A) were prepared so as to give a Ca/P molar ratio of 0.5. The aqueous solution of anhydrous sodium dihydrogen phosphate was placed in a stainless-steel beaker and heated to 80° C. with stirring. The pH was left at 4.2 and not adjusted. The calcium hydroxide slurry was added thereto for a period of 30 minutes. After completion of the addition, the mixture was further stirred for 1 hour, and then filtered and washed with water, followed by drying at 80° C., thereby obtaining fine hydroxyapatite particles (powder).

The obtained fine hydroxyapatite particles were measured for X-ray crystal diffraction and specific surface area, and observed for shape in the same manner as in Example 1.

Figure 11A:
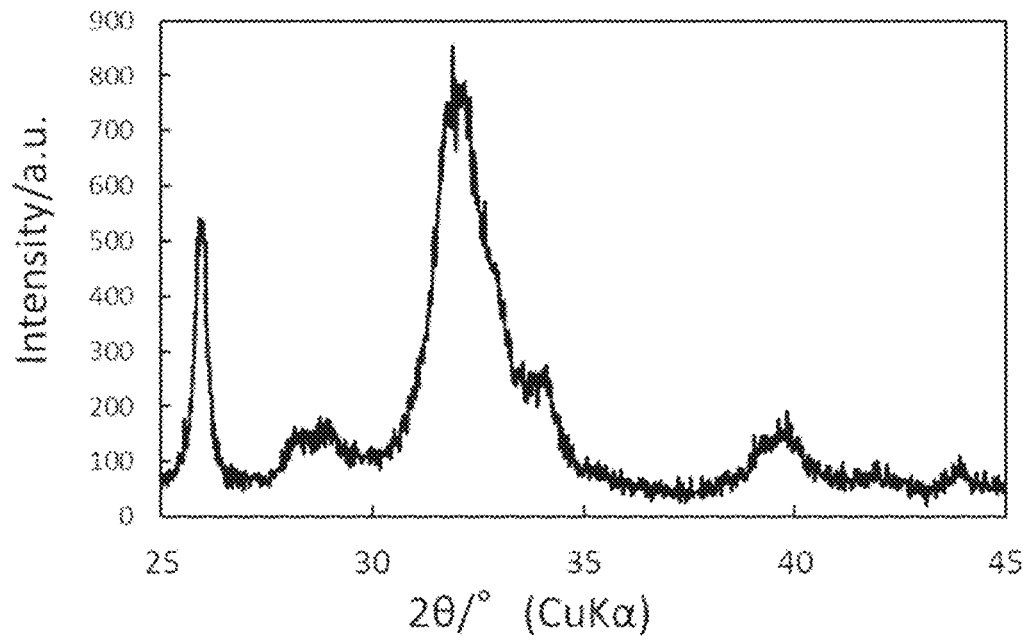
FIG. 11a shows the X-ray diffraction peaks of the fine hydroxyapatite particles in Example 6.

FIG. 11a shows the results of X-ray crystal diffraction. The ratio of the diffraction peak intensity of the (211) plane around 2θ=32° to the diffraction peak intensity of the (002) plane around 2θ=26° was 1.58. The sum of the areas of all of the diffraction peaks within the range of 25.5°≤2θ≤26.5° and the areas of all of the diffraction peaks within the range of 31.5°≤2θ≤32.5° was 40.9%, based on the sum of the areas of all of the diffraction peaks within the range of 25°≤2θ≤35° taken as 100%. The crystallite size calculated from the diffraction peak of the (130) plane around 2θ=40° was 7 nm.

The specific surface area was 105.0 m²/g.

Figure 11B:
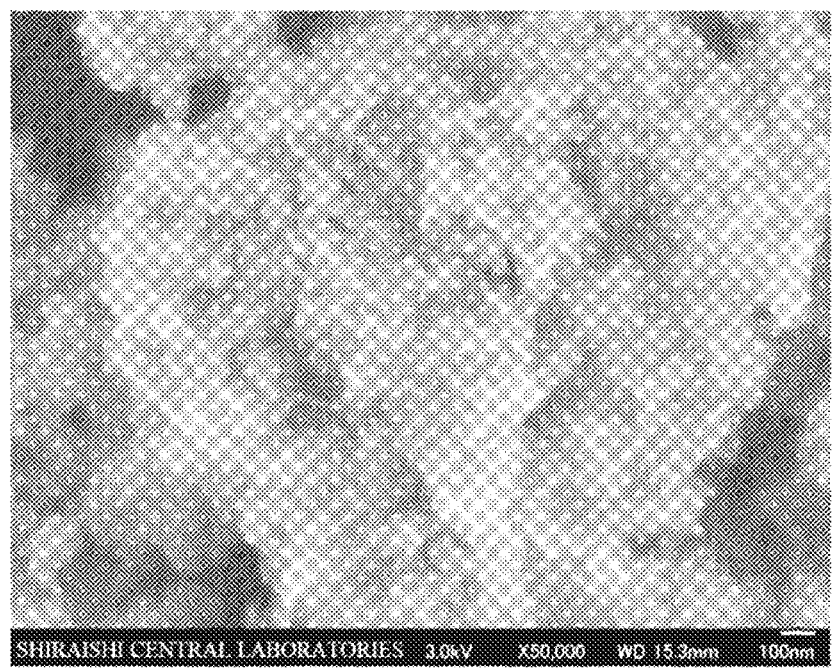
FIG. 11b shows an SEM photograph of the fine hydroxyapatite particles in Example 6.

FIG. 11b shows the results of shape observation. The results indicated that the obtained hydroxyapatite was in the form of aggregates of plate-like fine particles, as in Example 1.

Example 7

A 10.7 mass % aqueous solution of sodium dihydrogen phosphate-2 hydrate and a ground calcium hydroxide slurry with a solids concentration of 8.6 mass % (BET specific surface area: 6.7 m²/g, reactivity with oxalic acid: 15 minutes and 30 seconds, JP2017-036176A) were prepared so as to give a Ca/P molar ratio of 0.5. The aqueous solution of sodium dihydrogen phosphate-2 hydrate was placed in a stainless-steel beaker, and heated to 60° C. with stirring. This temperature was maintained until the end of stirring. A 10% aqueous solution of NaOH was added to adjust the pH to 5.5. The calcium hydroxide slurry was added thereto for a period of 30 minutes. After completion of the addition, the mixture was further stirred for 1 hour, and then filtered and washed with water, followed by drying at 80° C. After that, the mixture was allowed to stand at 40° C. and at 75% RH for 6 months, thereby obtaining fine hydroxyapatite particles (powder).

The obtained fine hydroxyapatite particles were measured for X-ray crystal diffraction and specific surface area, and observed for shape in the same manner as in Example 1.

Figure 11C:
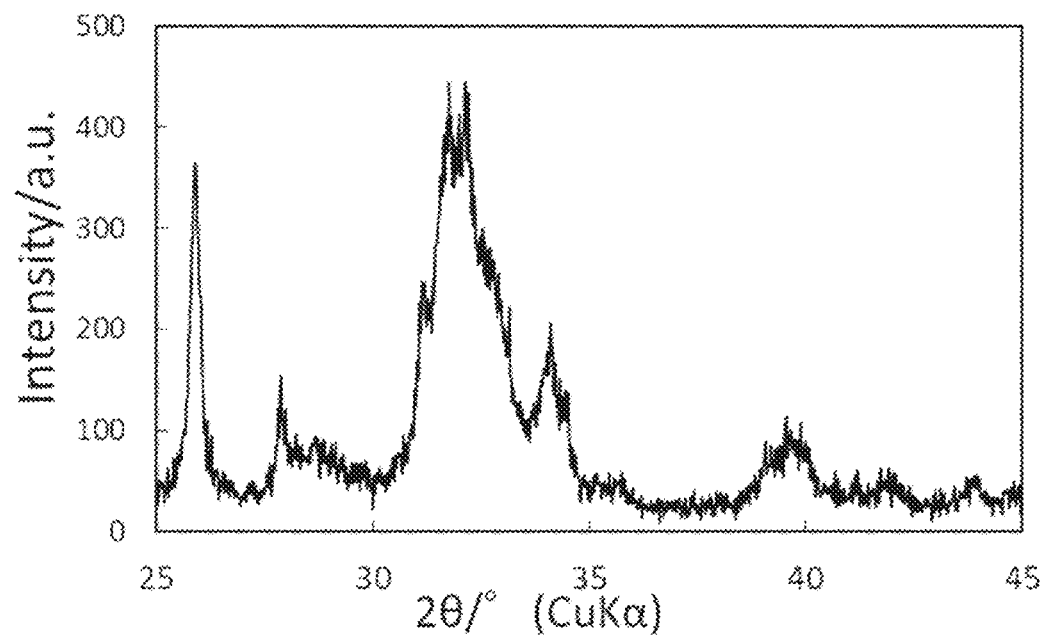
FIG. 11c shows the X-ray diffraction peaks of the fine hydroxyapatite particles in Example 7.

FIG. 11c shows the results of X-ray crystal diffraction. The ratio of the diffraction peak intensity of the (211) plane around 2θ=32° to the diffraction peak intensity of the (002) plane around 2θ=26° was 1.21. The sum of the areas of all of the diffraction peaks within the range of 25.5°≤2θ≤26.5° and the areas of all of the diffraction peaks within the range of 31.5°≤2θ≤32.5° was 39.4%, based on the sum of the areas of all of the diffraction peaks within the range of 25°≤2θ≤35° taken as 100%. The crystallite size calculated from the diffraction peak of the (130) plane around 2θ=400 was 8 nm.

The specific surface area was 34.8 m²/g.

Comparative Example 1

A 10.7 mass %, aqueous solution of anhydrous sodium dihydrogen phosphate and a ground calcium hydroxide slurry with a solids concentration of 8.6 mass % (BET specific surface area: 7.9 m²/g, reactivity with oxalic acid: 12 minutes and 30 seconds, JP2017-036176A) were prepared so as to give a Ca/P molar ratio of 0.5. The calcium hydroxide slurry was placed in a stainless-steel beaker and heated to 40° C. with stirring. The aqueous solution of anhydrous sodium dihydrogen phosphate (pH: 4.2) was added thereto for a period of 30 minutes. After completion of the addition, the mixture was further stirred for 1 hour, and then filtered and washed with water, followed by drying at 80° C., thereby obtaining hydroxyapatite particles (powder).

The obtained hydroxyapatite particles were measured for X-ray crystal diffraction and specific surface area, and observed for shape in the same manner as in Example 1.

Figure 12:
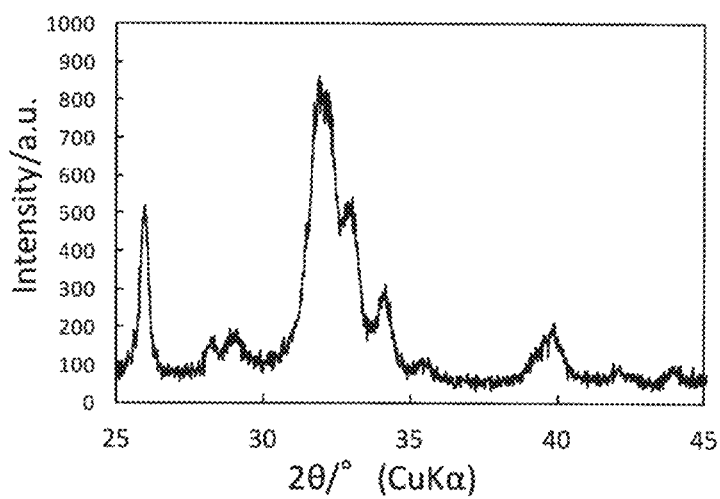
FIG. 12 shows the X-ray diffraction peaks of the hydroxyapatite particles in Comparative Example 1.

FIG. 12 shows the results of X-ray crystal diffraction. The ratio of the diffraction peak intensity of the (211) plane around 2θ=32° to the diffraction peak intensity of the (002) plane around 2θ=26° was 1.7, which was clearly higher than the value of Example 1. The diffraction peaks of the (300) plane around 2θ=33° appeared separately.

The specific surface area was 50.9 m/g.

Figure 13:
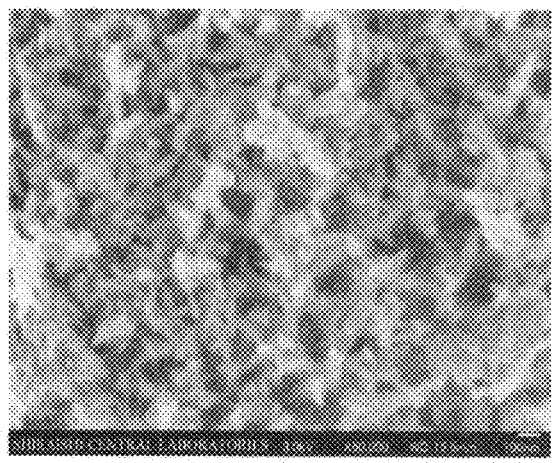
FIG. 13 shows an SEM photograph of the hydroxyapatite particles in Comparative Example 1.

FIG. 13 shows the results of shape observation. The results indicated that the obtained hydroxyapatite particles were in the form of aggregates of spindle-like crystals.

Comparative Example 2

A 10.7 mass % aqueous solution of sodium dihydrogen phosphate-2 hydrate and a ground calcium hydroxide slurry with a solids concentration of 8.6 mass % (JP2017-036176A) were prepared so as to give a Ca/P molar ratio of 0.5. The aqueous solution of sodium dihydrogen phosphate-2 hydrate was placed in a stainless-steel beaker and heated to 60° C. with stirring. This temperature was maintained until the end of stirring. The pH was left at 4.2 and not adjusted. The calcium hydroxide slurry was added thereto for a period of 45 minutes. After completion of the addition, the mixture was further stirred for 1 hour, and then filtered and washed with water, followed by drying at 80° C., thereby obtaining a sample.

The obtained sample was measured for X-ray crystal diffraction and observed for shape in the same manner as in Example 1.

Figure 14:
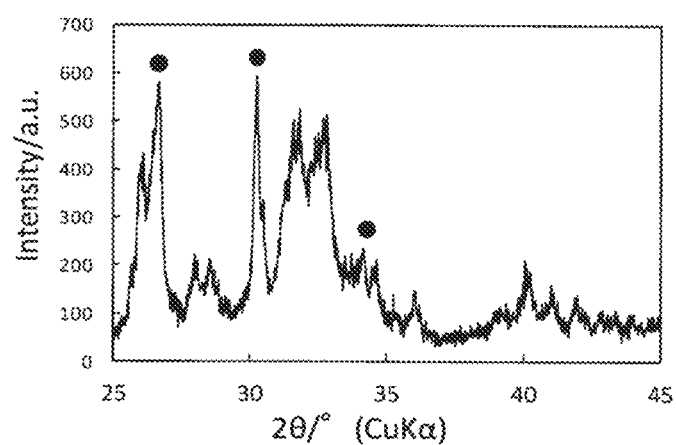
FIG. 14 shows the X-ray diffraction peaks of the sample in Comparative Example 2. The peaks indicated by a solid black circle are diffraction peaks of monetite.

FIG. 14 shows the results of X-ray crystal diffraction. Diffraction peaks of other substances were confirmed. The peaks indicated by solid black circles in FIG. 14 are diffraction peaks of monetite, which is calcium phosphate that tends to form under acidic conditions.

Figure 15:
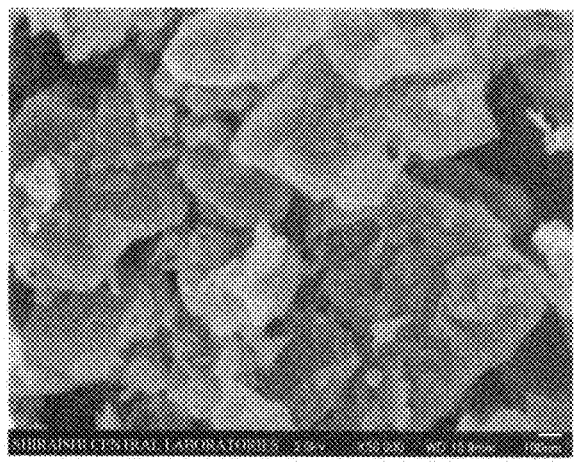
FIG. 15 shows an SEM photograph of the sample in Comparative Example 2.

FIG. 15 shows the results of shape observation. Large plate-like particles of monetite were confirmed.

Comparative Example 3

A 10.7 mass % aqueous solution of sodium dihydrogen phosphate-2 hydrate and a high-purity calcium hydroxide slurry with a solids concentration of 8.6 mass % (BET specific surface area: 2.4 m²/g, reactivity with oxalic acid: 25 seconds, JP2011-126772A) were prepared so as to give a Ca/P molar ratio of 0.5. The aqueous solution of sodium dihydrogen phosphate-2 hydrate was placed in a stainless-steel beaker and heated to 60° C. with stirring. This temperature was maintained until the end of stirring. A 10 aqueous solution of NaOH was added to adjust the pH to 5.5. The calcium hydroxide slurry was added thereto for a period of 30 minutes. After completion of the addition, the mixture was further stirred for 1 hour, and then filtered and washed with water, followed by drying at 80° C., thereby obtaining a sample.

The obtained sample was measured for X-ray crystal diffraction in the same manner as in Example 1.

Figure 16:
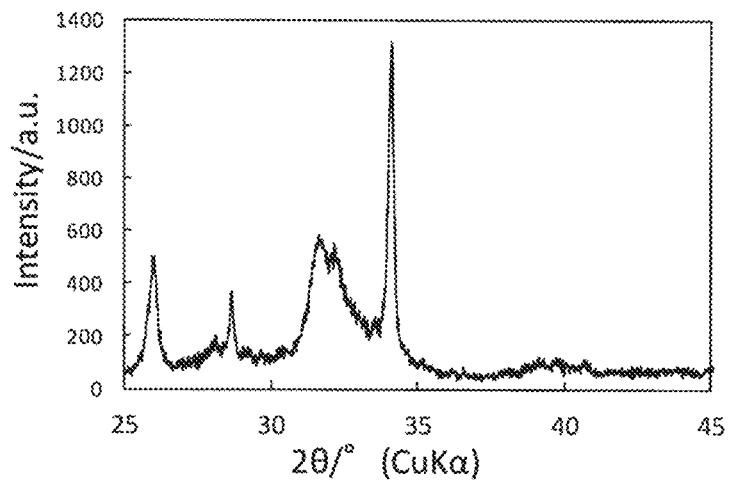
FIG. 16 shows the X-ray diffraction peaks of the sample in Comparative Example 3.

FIG. 16 shows the results of X-ray crystal diffraction. In addition to the diffraction peaks of hydroxyapatite, the diffraction peaks of calcium hydroxide were confirmed around 2θ=28° and around 2θ=34°.

Figure 17:
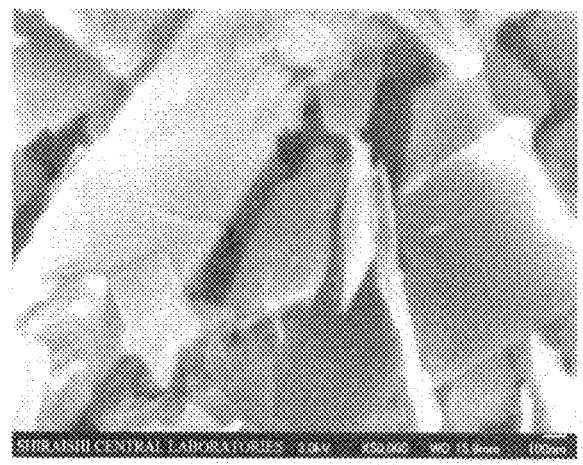
FIG. 17 shows an SEM photograph of the sample in Comparative Example 3.

FIG. 17 shows the results of shape observation. Large plate-like particles of calcium hydroxide were confirmed. The difference from Example 1 was speculated to be due to the physical properties of the calcium hydroxide used as a starting material.

Example 8

A 10.7 mass % aqueous solution of sodium dihydrogen phosphate-2 hydrate and a ground calcium hydroxide slurry with a solids concentration of 8.6 mass % (BET specific surface area: 7.9 m$^2$/g, reactivity with oxalic acid: 12 minutes and 30 seconds, JP2017-036176A) were prepared so as to give a Ca/P molar ratio of 0.5. The aqueous solution of sodium dihydrogen phosphate-2 hydrate was placed in a stainless-steel beaker, and a 10% aqueous solution of NaOH was added thereto to adjust the pH to 5.5. The calcium hydroxide slurry was then added thereto for a period of 50 minutes. After completion of the addition, the mixture was further stirred for 1 hour. After stirring was ended, the reaction mixture was allowed to stand at room temperature for 9 days, and then filtered and washed with water, followed by drying at 80° C., thereby obtaining hydroxyapatite particles (powder).

The obtained hydroxyapatite particles were measured for X-ray crystal diffraction and observed for shape in the same manner as in Example 1.

Figure 18:
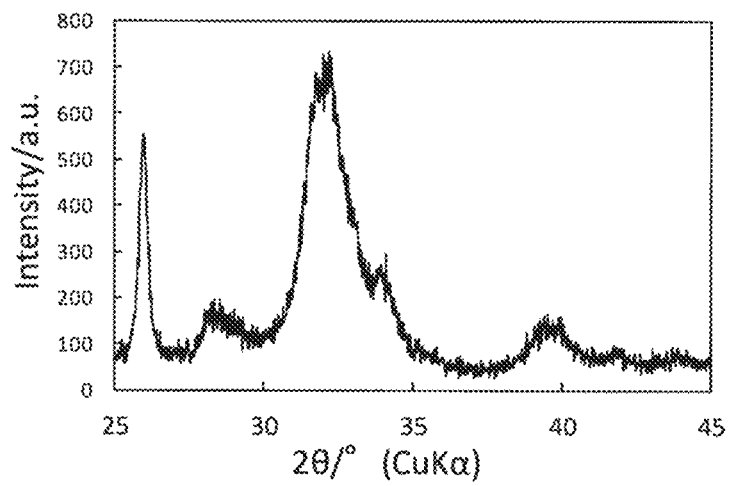
FIG. 18 shows the X-ray diffraction peaks of the hydroxyapatite particles in Example 8.

FIG. 18 shows the results of X-ray crystal diffraction. The ratio of the diffraction peak intensity of the (211) plane around 2θ=32° to the diffraction peak intensity of the (002) plane around 2θ=26° was 1.3.

Figure 19:
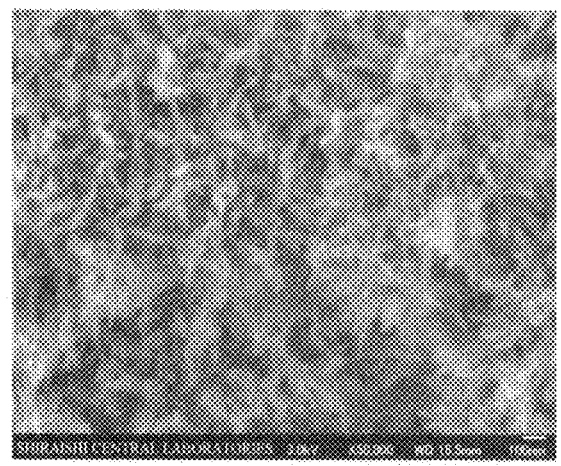
FIG. 19 shows an SEM photograph of the hydroxyapatite particles in Example 8.

FIG. 19 shows the results of shape observation. The shape of the particles was confirmed to be an aggregate of microscopic spindle-shaped particles.

Comparative Example 4

A 10.7 mass %, aqueous solution of sodium dihydrogen phosphate-2 hydrate and a ground calcium hydroxide slurry with a solids concentration of 8.6 mass (JP2017-036176A) were prepared so as to give a Ca/P molar ratio of 0.5. The aqueous solution of sodium dihydrogen phosphate-2 hydrate was placed in a stainless-steel beaker and heated to 80° C. with stirring. This temperature was maintained until the end of stirring. The pH was left at 4.2 and not adjusted. The calcium hydroxide slurry was added thereto for a period of 50 minutes. After completion of the addition, the mixture was further stirred for 1 hour, and then filtered and washed with water, followed by drying at 80° C., thereby obtaining a sample.

The obtained sample was measured for X-ray crystal diffraction and observed for shape in the same manner as in Example 1.

Figure 20:
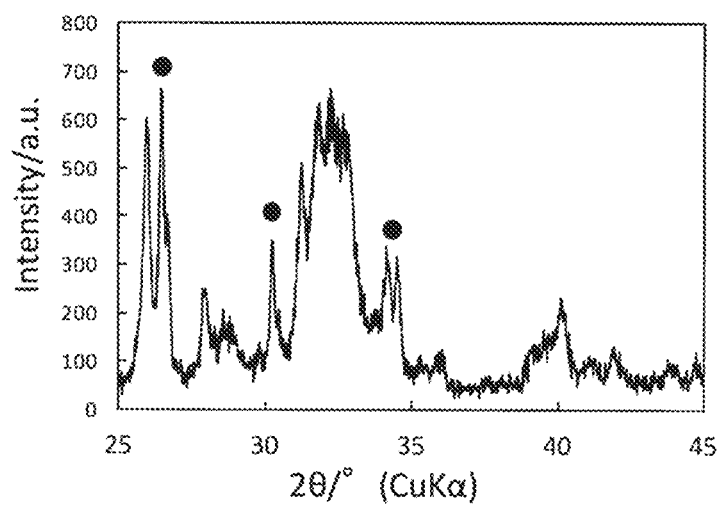
FIG. 20 shows the X-ray diffraction peaks of the sample in Comparative Example 4. The peaks indicated by a solid black circle are diffraction peaks of monetite.

FIG. 20 shows the results of X-ray crystal diffraction. The diffraction peaks of other substances were confirmed. The peaks indicated by solid black circles are diffraction peaks of monetite, which is calcium phosphate that tends to form under acidic conditions.

Figure 21:
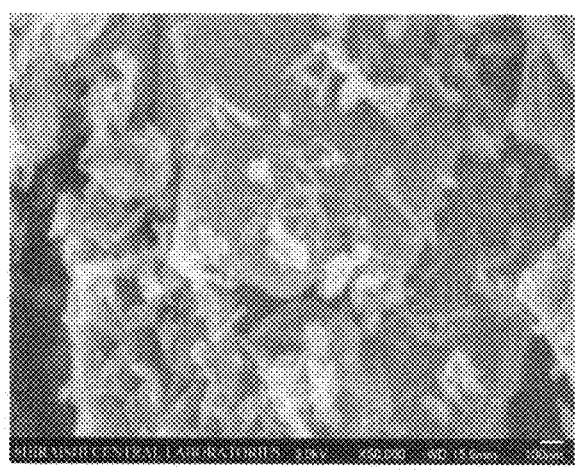
FIG. 21 shows an SEM photograph of the sample in Comparative Example 4.

FIG. 21 shows the results of shape observation. Large plate-like particles of monetite were confirmed.

Test Example 1: Crystallinity Change Confirmation Test

Test Purpose

To evaluate the reactivity of hydroxyapatite particles in the oral cavity, changes in crystallinity before and after immersion in artificial saliva were measured with a powder X-ray diffractometer.

Test Method 0.5 g of hydroxyapatite particles obtained in the same manner as in Example 1 were immersed in 200 mL of artificial saliva ($CaCl_2$: 1.5 mM; $KH_2PO_4$: 0.9 mM; KCl: 130 mM; HEPES: 20 mM; pH 7.0 (KOH)) for 7 days. Powder separated by suction filtration was measured with a powder X-ray diffractometer, and changes in crystallinity before and after immersion in artificial saliva were observed.

Measurement Conditions

Model used: MiniFlex II (Rigaku Corporation)
Start angle: 20°
End angle: 40°
Sampling range: 0.02°
Scanning rate: 4.0°/min
Target: Cu
Tube voltage: 30 kV
Tube current: 15 mA
Divergence slit: 1.25°
Scatter slit: 8.0 mm
Light-receiving slit: 0.3 mm.

Figure 22:
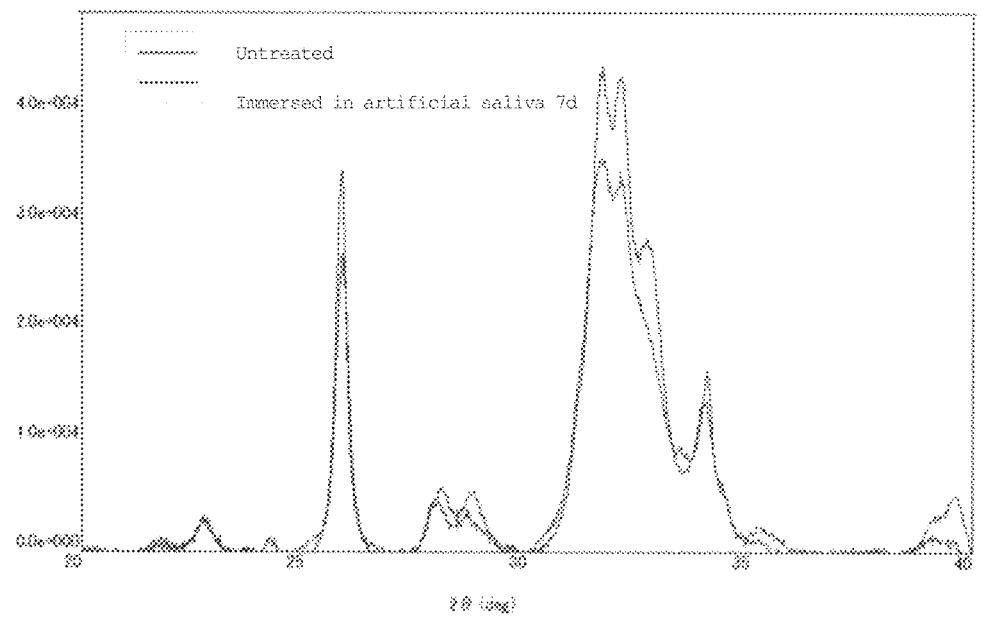
FIG. 22 shows the X-ray diffraction peaks of hydroxyapatite particles before and after being immersed in artificial saliva (Test Example 1).

FIG. 22 shows the results. The immersion in artificial saliva was confirmed to have improved crystallinity (increased peak sharpness and appearance of broad, hidden peaks). This indicates that the hydroxyapatite particles change in the oral cavity (i.e., they are reactive).

The same study was performed by using known hydroxyapatite particles instead of hydroxyapatite particles obtained in the same manner as in Example 1. No change was observed in the peaks before and after immersion in artificial saliva, with no change in crystallinity.

Test Example 2: Test on Properties to Seal Dentinal Tubules of Hydroxyapatite Particles Test Purpose To evaluate the ability of hydroxyapatite particles to seal dentinal tubules, the surface of bovine dentin was brushed with a solution of hydroxyapatite particles, and the degree of dentinal tubule sealing was examined by observation with an electron microscope (SEM).

Test Method

Preparation of Dentin Block (Sample)

1. The dentin on the root surface of an extracted bovine tooth was cut out to a size of 5×5 mm.
2. The cut tooth fragment was embedded in resin (polymethyl methacrylate) to prepare a block, followed by polishing the block with waterproof abrasive paper to expose the surface.
3. The dentin block was immersed in a 5% w/w aqueous EDTA solution (pH 7.0) for 2 minutes.
4. Sonication was performed in distilled water for 5 minutes.

Preparation of Liquid of Hydroxyapatite Particles 5. 0.3 g of hydroxyapatite particles obtained in the same manner as in Example 1 were suspended in 39.7 g of a viscous diluent, thereby obtaining a liquid of hydroxyapatite particles. The viscous diluent was an aqueous solution containing 0.5 w/w % sodium carboxymethyl cellulose and 10 w/w % glycerol.

Brushing Treatment

6. The dentin block was brushed in the liquid of hydroxyapatite particles (40 g) for 30 seconds with a toothbrush (GUM #211) (stroke: 150 rpm, load: 160 g).

7. After the dentin block was washed with water, the block was immersed in artificial saliva ($CaCl_2$): 1.5 mM; $KH_2PO_4$: 0.9 mM; KCl: 130 mM; HEPES: 20 mM; pH 7.0 (KOH)) for 5 minutes.

8. Operations 1 and 2 above were performed 6 times.

Observation with SEM

9. The surface was vapor-deposited and observed with an electron microscope.

Conditions of Observation and Measurement

Vapor Deposition
- Model used: MCI1000 (Hitachi High-Tech Corporation)
- Current: 20 mA
- Treatment time: 120 seconds Observation with SEM
- Model used: S-3400N (Hitachi High-Tech Corporation)
- Detector: SE (secondary electron image)
- Applied voltage: 5 kV
- Probe current: 50 mA
- Magnification: 25000×

Figure 23:
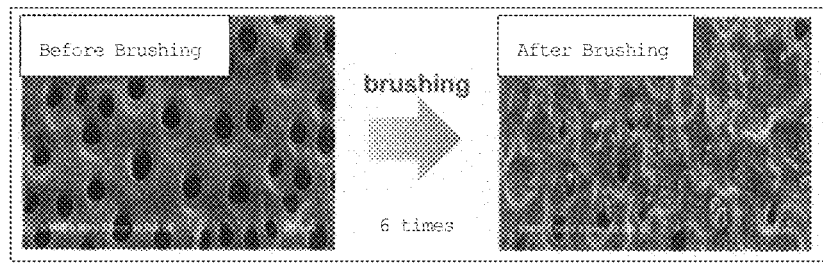
FIG. 23 shows SEM photographs of dentinal tubules before and after being brushed (Test Example 2).

FIG. 23 shows the results. Dentinal tubules were confirmed to have been sealed by brushing in the liquid of hydroxyapatite particles. This indicates that the hydroxyapatite particles seal the dentinal tubules present on the surface of dentin.

Test Example 3: Adhesion Properties Test

Test Purpose

To evaluate the ability of hydroxyapatite particles to adhere in dentinal tubules, the surface of bovine dentin was brushed with a liquid of hydroxyapatite particles, and then water pressure was applied from the back of dentin. Whether the sealing of hydroxyapatite particles withstood the water pressure was examined by observation with an electron microscope (SEM).

Test Method

Preparation of Dentin Disc (Sample)

1. The dentin on the root surface of an extracted bovine tooth was cut out to a size of 5×5 mm.

2. The cut tooth fragment was polished with waterproof abrasive paper.

3. The obtained dentin disc was immersed in a 5 w/w aqueous EDTA solution (pH 7.0) for 2 minutes.

4. Sonication was performed in distilled water for 5 minutes.

Preparation of Liquid of Hydroxyapatite Particles 5. 1 g of hydroxyapatite particles obtained in the same manner as in Example 1 were suspended in 39 g of a viscous diluent, thereby obtaining a liquid of hydroxyapatite particles. The viscous diluent was an aqueous solution containing 0.5 w/w % sodium carboxymethyl cellulose and 10 w/w % glycerol.

Brushing

6. A dentin disc was brushed in the liquid of hydroxyapatite particles (40 g) for 30 seconds with a toothbrush (GUM #211) (stroke: 150 rpm, load: 160 g).

7. The disc was washed with water and immersed in artificial saliva ($CaCl_2$): 1.5 mM; $KH_2PO_4$: 0.9 mM; KCl: 130 mM; HEPES: 20 mM; pH 7.0 (KOH)) for 5 minutes.

8. Operations 1 and 2 above were performed 6 times.

9. The disc was immersed in artificial saliva for 7 days.

Water Pressure

10. Pressure was applied at 0.1 MPa for 30 minutes to a dentin disc that was brushed beforehand, by using an instrument with reference to a report by Pashley et al. (Pashley D H, Galloway S E. The effects of oxalate treatment on the smear layer of ground surfaces of human dentin. Arch. Oral Biol. 1983; 30: 731-737).

Observation with SEM

11. The surface was vapor-deposited and observed with an electron microscope.

Conditions of Observation and Measurement

Vapor Deposition
- Model used: MCI1000 (Hitachi High-Tech Corporation)
- Current: 20 mA
- Treatment time: 120 seconds Observation with SEM
- Model used: S-3400N (Hitachi High-Tech Corporation)
- Detector: SE (secondary electron image)
- Applied voltage: 5 kV
- Probe current: 50 mA
- Magnification: 25000×

Figure 24:
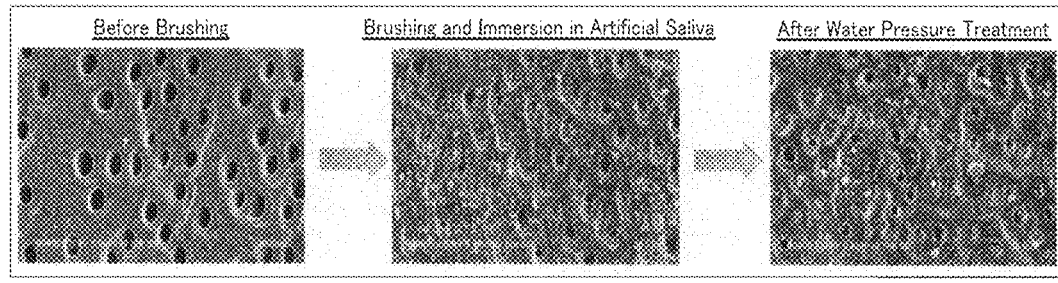
FIG. 24 shows SEM photographs of dentinal tubules before and after water-pressure treatment (Test Example 3).

FIG. 24 shows the results. The dentinal tubules were confirmed to have been sealed after water-pressure treatment. This indicates that the hydroxyapatite particles adhere within dentinal tubules and continue to seal dentinal tubules.

Test Example 4: Test on Properties to Seal Dentinal Tubules of Dentifrice

Test Purpose

To confirm the ability to seal dentinal tubules of a material-containing dentifrice preparation, the surface of bovine dentin was brushed with a material solution, and the degree of dentinal tubule sealing was examined by observation with an electron microscope (SEM).

Test Method

Preparation of Dentin Block (Sample)

1. The dentin on the root surface of an extracted bovine tooth was cut out to a size of 5×5 mm.

2. The cut tooth fragment was embedded in resin (polymethyl methacrylate) to prepare a block, followed by polishing the block with waterproof abrasive paper to expose the surface.

3. The dentin block was immersed in a 5% w/w aqueous EDTA solution (pH 7.0) for 2 minutes.

4. Sonication was performed in distilled water for 5 minutes.

Preparation of Dentifrice Solution 5. 10 g of a dentifrice containing 3 w/w % hydroxyapatite particles that were obtained in the same manner as in Example 1 was prepared in accordance with an ordinary method. Table 1 below shows the formulation of the dentifrice. The unit "%" for the amount of components in the tables below indicates mass %.

TABLE 1

| Component | Amount (%) |
| --- | --- |
| Hydroxyapatite | 3 |
| Potassium Nitrate | 5 |
| Aluminum Lactate | 2.2 |

TABLE 1-continued

| Component | Amount (%) |
|---|---|
| Concentrated Glycerin | 17 |
| Sorbitol Liquid | 23 |
| Silicic Anhydride | 14 |
| Sodium Carboxymethyl Cellulose | 1 |
| Xanthan Gum | 0.5 |
| Dipotassium Glycyrrhizinate | 0.02 |
| Sodium Lauryl Sulfate | 1.1 |
| Polyoxyethylene Hydrogenated Castor Oil | 0.5 |
| Sodium Monofluorophosphate | 1.1 |
| Saccharin Sodium | 0.1 |
| Paraoxybenzoic Acid Ester | 0.2 |
| Sodium Hydroxide | 0.5 |
| Titanium Oxide | 0.3 |
| Flavoring Agent | 1.0 |
| Purified Water | Balance |

Figure 25:
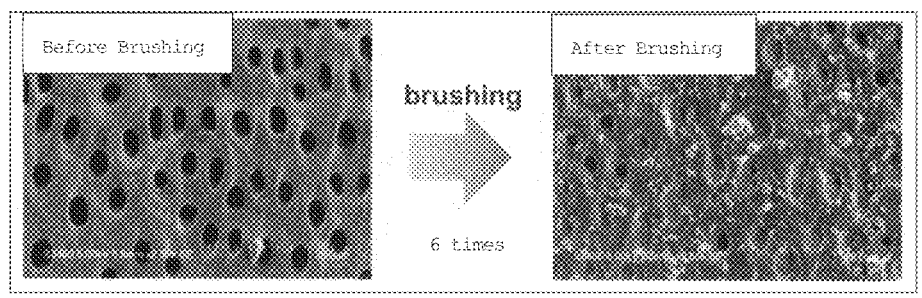
FIG. 25 shows SEM photographs of dentinal tubules before and after brushing by using a dentifrice solution containing hydroxyapatite particles (Test Example 4).

Brushing
6. 10 g of the dentifrice was diluted 4-fold with distilled water, thereby obtaining a dentifrice solution. The dentin block was brushed in the dentifrice solution (40 g) for 30 seconds with a toothbrush (GUM #211) (stroke: 150 rpm, load: 160 g).
7. After the dentin block was washed with water, the block was immersed in artificial saliva ($CaCl_2$: 1.5 mM; $KH_2PO_4$: 0.9 mM; KCl: 130 mM; HEPES: 20 mM; pH 7.0 (KOH)) for 5 minutes.
8. Operations 1 and 2 above were performed 6 times.
Observation with SEM
9. The surface was vapor-deposited and observed with an electron microscope.
Conditions of Observation and Measurement
Vapor Deposition
    Model used: MCI1000 (Hitachi High-Tech Corporation)
    Current: 20 mA
    Treatment time: 120 seconds
Observation with SEM
    Model used: S-3400N (Hitachi High-Tech Corporation)
    Detector: SE (secondary electron image)
    Applied voltage: 5 kV
    Probe current: 50 mA
    Magnification: 25000×
FIG. 25 shows the results. Dentinal tubules were confirmed to have been sealed by brushing in the dentifrice solution containing hydroxyapatite particles. This indicates that the dentifrice containing hydroxyapatite particles is highly effective in sealing dentinal tubules.

Test Example 5: Test on Properties to Seal Dentinal Tubules of Gel Preparation Applied with Soft-Pick Test Purpose
To confirm the ability to seal dentinal tubules of a gel preparation containing hydroxyapatite particles, a gel preparation was applied to the surface of bovine dentin with a Soft-pick (interdental brush made from rubber), and the degree of dentinal tubule sealing was examined by observation with an electron microscope (SEM).
Test Method
Preparation of Dentin Block (Sample)
1. The dentin on the root surface of an extracted bovine tooth was cut out to a size of 5-5 nm.
2. The cut tooth fragment was embedded in resin (polymethyl methacrylate) to prepare blocks, followed by polishing the blocks with waterproof abrasive paper to expose the surface.
3. The dentin blocks were immersed in a 5% w/w aqueous EDTA solution (pH 7.0) for 2 minutes.
4. Sonication was performed in distilled water for 5 minutes.
5. Two dentin blocks were fixed with tape so as to face each other with space of 1.1 mm between the dentin surfaces to form a pseudo-interdental space.
Application
6. A gel preparation containing (or not containing) hydroxyapatite particles obtained in the same manner as in Example 1 was placed on the brush portion of a Soft-pick (Gum Soft-picks, curved: Sunstar Inc.). The Soft-pick was inserted into the space and moved back and forth 5 times. Table 2 below shows the formulation of the gel preparation.
7. The dentin blocks were washed with water.

TABLE 2

| | Amount (%) | |
|---|---|---|
| Component | Placebo | HAp 5% |
| Hydroxyapatite | 0 | 5 |
| Potassium Nitrate | 5 | 5 |
| Aluminum Lactate | 2.2 | 2.2 |
| Concentrated Glycerin | 37 | 37 |
| Sorbitol Liquid | 13 | 13 |
| Silicic Anhydride | 3 | 3 |
| Sodium Carboxymethyl Cellulose | 1 | 7 |
| Xanthan Gum | 0.5 | 0.5 |
| Propylene Glycol | 3 | 3 |
| Polyoxyethylene Hydrogenated Castor Oil | 1 | |
| Sodium Monofluorophosphate | 1.1 | 1.1 |
| Saccharin Sodium | 0.1 | 0.1 |
| Paraoxybenzoic Acid Ester | 0.2 | 0.2 |
| Sodium Monohydrogen Phosphate | 0.5 | 0.5 |
| Sodium Hydroxide | 0.7 | 0.7 |
| Mixed Pigment (Diisostearyl Malate 70%, Legally Permitted Pigment 30%) | 0.005 | 0.005 |
| Titanium Oxide | 0.3 | 0.3 |
| Flavoring Agent | 0.98 | 0.98 |
| Purified Water | Balance | Balance |

Figure 26:
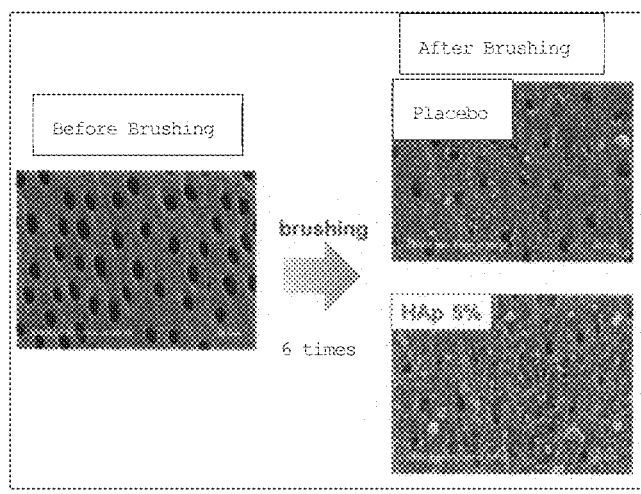
FIG. 26 shows SEM photographs of dentinal tubules before and after a gel preparation containing hydroxyapatite particles was applied to dentin with a Soft-pick (Test Example 5).

Observation with SEM
8. The surface was vapor-deposited and observed with an electron microscope.
Conditions of Observation and Measurement
Vapor Deposition
    Model used: MCI1000 (Hitachi High-Tech Corporation)
    Current: 20 mA
    Treatment time: 120 seconds
Observation with SEM
    Model used: S-3400N (Hitachi High-Tech Corporation)
    Detector: SE (secondary electron image)
    Applied voltage: 5 kV
    Probe current: 50 mA
    Magnification: 25000×
FIG. 26 shows the results. Dentinal tubules were confirmed to have been sealed by applying the gel preparation containing hydroxyapatite particles with a Soft-pick.

Test Example 6: Gel Preparation Clinical Trial

Test Purpose
The clinical efficacy in anti-hypersensitivity of a gel preparation containing hydroxyapatite particles was studied. In this study, hydroxyapatite particles prepared in the same manner as in Example 1 were used as hydroxyapatite particles.

Test Design

A comparison was made between the following three preparations:
(i) A gel preparation containing hydroxyapatite particles, aluminum lactate, and potassium nitrate (HAp+Al+K), (ii) a gel preparation containing aluminum lactate and potassium nitrate (Al+K), and (iii) a gel preparation containing potassium nitrate (K). Table 3 below shows the formulations of these gel preparations.

TABLE 3

| Component | Amount (%) | | |
|---|---|---|---|
| | HAp + AL + K | Al + K | K |
| Hydroxyapatite | 5 | 0 | 0 |
| Aluminum Lactate | 2.2 | 2.2 | 0 |
| Potassium Nitrate | 5 | 5 | 5 |
| Concentrated Glycerin | 37 | 37 | 37 |
| Sorbitol Liquid | 13 | 13 | 13 |
| Silicic Anhydride | 3 | 3 | 3 |
| Sodium Carboxymethyl Cellulose | 1 | 1 | 1 |
| Xanthan Gum | 0.5 | 0.5 | 0.5 |
| Propylene Glycol | 3 | 3 | 3 |
| Polyoxyethylene Hydrogenated Castor Oil | 1 | | 1 |
| Sodium Monofluorophosphate | 1.1 | 1.1 | 1.1 |
| Saccharin Sodium | 0.1 | 0.1 | 0.1 |
| Paraoxybenzoic Acid Ester | 0.2 | 0.2 | 0.2 |
| Sodium Monohydrogen Phosphate | 0.5 | 0.5 | 0.5 |
| Sodium Hydroxide | 0.7 | 0.7 | 0.7 |
| Mixed Pigment (Diisostearyl Malate 70%, Legally Permitted Pigment 30%) | 0.005 | 0.005 | 0.005 |
| Titanium Oxide | 0.3 | 0.3 | 0.3 |
| Flavoring Agent | 0.98 | 0.98 | 0.98 |
| Purified Water | Balance | Balance | Balance |

Figure 27:
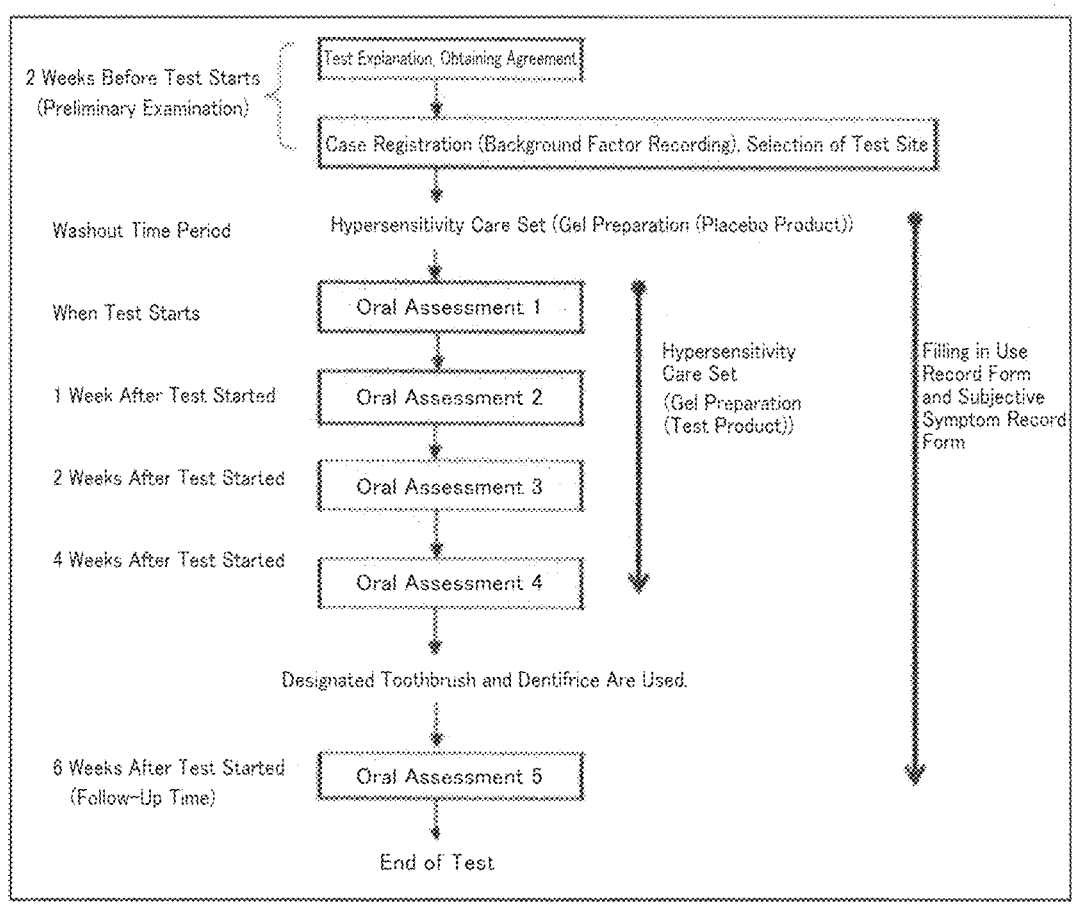
FIG. 27 shows a flowchart of a clinical trial using a gel preparation containing hydroxyapatite particles.

These gel preparations were each used by 20 subjects. At a point of 1, 2, or 4 weeks after use, the subjects were asked to describe the intensity of rubbing pain on a VAS scale (a probe was applied to the exposed root surface, and the surface was rubbed horizontally with the probe). The VAS scale is a visual scale; a 10-cm black line (the left end indicating no pain at all and the right end indicating most tingling or severe pain) is shown to a patient, and the patient points to the intensity of current pain on the scale. FIG. 27 shows the flowchart of this test. In FIG. 27, "Hypersensitivity Care Set (Gel Preparation (Test Product))" indicates gel preparations (i) to (iii) above, and "Hypersensitivity Care Set (Gel Preparation (Placebo Product))" indicates a gel preparation formed by removing potassium nitrate from gel preparation (iii).

Method for Using Test Product

Subjects were asked to use a gel preparation (test product) twice a day (morning and evening; when the subjects should use a gel preparation, such as after waking up, after a meal, or before going to bed, was not specified; the subjects were allowed to use the preparation on the basis of their habitual oral cleaning). Specifically, first, the subjects were asked to brush their teeth with a designated toothbrush (G.U.M Pro's Dental Brush #3c; Sunstar Inc.) and a dentifrice (CO-OP non-foaming toothpaste N), to rinse their mouth with about 10 mL of water for 20 seconds (the brushing time period was not specified), and then to use a gel preparation. For the way to use the gel preparation, specifically, the subjects were asked to apply about 0.04 g of a gel preparation (test product; about the size of a rice grain) per test tooth to a test site with a tuft brush (Butler single-tuft brush #01F: Sunstar Inc.), and brush the test site and the two teeth next to the test site for at least 5 seconds per tooth. If a designated interdental cleaning tool (Gum Soft-picks, curved: Sunstar Inc.) could be inserted into the space between the test site and the next teeth, the interdental cleaning tool was inserted into the space between the test site and the next teeth from the cheek side, and the tool was moved back and forth 5 times. After using the gel preparation (test product), the subjects were asked to rinse their mouth with about 10 mL of water for 20 seconds.

Figure 28:
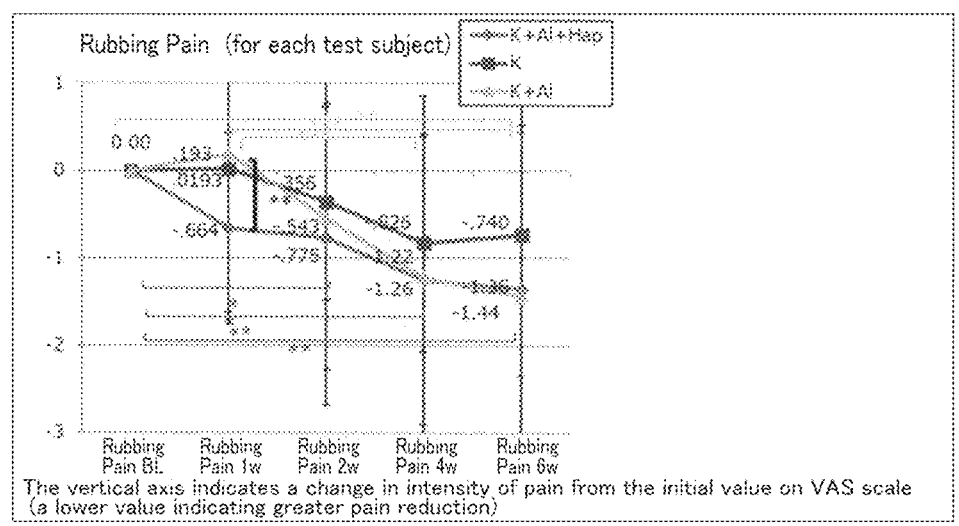
FIG. 28 shows the results of evaluating the degree of rubbing pain on the VAS scale in a clinical trial using a gel preparation containing hydroxyapatite particles.

FIG. 28 shows the results of evaluating the intensity of rubbing pain on a VAS scale. At a point of one week after the start of using the preparation, the group of subjects who used the hydroxyapatite-containing preparation exhibited significant improvement in rubbing pain, as compared with the group of subjects who used the preparation containing no hydroxyapatite. This indicates that the hydroxyapatite-containing preparation is effective in reducing hypersensitivity symptoms at an early stage when used in combination with aluminum lactate and/or potassium nitrate, which are known medicinal ingredients for preventing hypersensitivity.

Test Example 7: Study on Oral Composition Containing Hydroxyapatite Particles and Silica Particles An oral composition was prepared by using hydroxyapatite particles prepared in the same manner as in Example 1 (HAp produced in accordance with the procedure in Example 1) or commercially available hydroxyapatite particles (commercially available HAp, produced by Tomita Pharmaceutical Co., Ltd.; commercially available hydroxyapatite different from the above reagent HAp) with commercially available silica (silica a or silica b: both precipitated silica). Specifically, the components described in Table 4A and Table 4B were mixed to prepare oral compositions. The values of the components shown in Table 4A and Table 4B are indicated in mass %. The mean particle size of silica a is 2.4 μm, and the mean particle size of silica b is 17 μm. The pH of silica (5 aq. sol.; i.e., the pH determined with 5 g of silica dispersed in 95 mL of purified water) is the following: pH of silica a, 6.7; pH of silica b, 5.5 to 7.5. The HAp produced in accordance with the procedure in Example 1 and commercially available HAp were measured for X-ray crystal diffraction in the same manner as in Example 1. The ratio of the diffraction peak intensity of the (211) plane around $2\theta=32°$ to the diffraction peak intensity of the (002) plane around $2\theta=26°$ was 1.44 in the HAp produced in accordance with the procedure in Example 1, and 2.72 in the commercially available HAp.

The oral compositions obtained in accordance with the formulations shown in Table 4A were examined for the period of time until the oral compositions dropped off after each composition was placed on a toothbrush, and the toothbrush was turned over. In more detail, 25 g of each oral composition was placed in a laminate tube (aperture diameter: 8 mm), and the tubes were stored at room temperature (about 25° C.) or at 55° C. in a dark room for two months. The oral compositions stored at 55° C. were brought back to room temperature. The oral compositions were pushed out; about 0.5 g of each oral composition was weighed with an electronic balance and placed on a toothbrush (G.U.M Dental Brush #211M: Sunstar Inc.). The period of time was measured until the oral composition dropped off the toothbrush after the toothbrush was turned over at a height of 2.5 cm so that the bristles faced downward. The period of time was determined to be the time required for dropping off. Table 4A also shows the results of this study.

TABLE 4A

|  |  | Using Silica a | | | Using Silica b | | |
| --- | --- | --- | --- | --- | --- | --- | --- |
|  |  | Comparative Example 1a | Example 1a | Comparative Example 2a | Comparative Example 1b | Example 1b | Comparative Example 2b |
| Silica |  |  | 15 |  |  | 5 |  |
| HAp produced in accordance with the procedure of Example 1 |  | — | 5 | — | — | 5 | — |
| Commercially Available HAp |  | — | — | 5 | — | — | 5 |
| Potassium Nitrate |  | 5 | | | | | |
| Water |  | 20.2 | | | | | |
| Saccharin Sodium |  | 0.12 | | | | | |
| Polyoxyethylene Hydrogenated Castor Oil |  | 1 | | | | | |
| 70% Sorbitol Liquid |  | 13.2 | | | | | |
| Methyl Benzoate |  | 0.2 | | | | | |
| Sodium Carboxymethyl Cellulose |  | 1.8 | | | | | |
| Flavoring Agent |  | 0.98 | | | | | |
| Glycerol |  | Balance | | | | | |
| Room Temperature | Time Required for Dropping Off (seconds) | 10 | >180 | 20 | 10 | >180 | 120 |
| 55° C. | Time Required for Dropping Off (seconds) | >180 | >180 | >180 | 30 | >180 | 50 |

The results indicate that the use of the specific hydroxyapatite particles obtained in the Examples in combination with silica provides an oral composition the dropping off of which from a toothbrush is suppressed with improved usability.

Additionally, the oral compositions obtained in accordance with the formulations shown in Table 4B were stored at 55° C. in a dark room for a long period of time, and then the water separation percentage and whiteness were determined in the following manner.

Water Separation Percentage

At least 60 mL of each obtained oral composition was placed in a colorless and transparent glass container (produced by Hakuyo Glass Co., Ltd.), and allowed to stand at 55° C. in a dark room for 4 months, followed by visually observing each specimen. When water separation was observed, the water separation percentage was calculated from the following formula: (the water separation percentage)=the height of an aqueous layer/the height of the composition.

Whiteness 25 g of each obtained oral composition (aperture diameter: 8 mm) was placed in a laminate tube and stored at 55° C. in a dark room for 4 months. Thereafter, the oral compositions in laminate tubes were brought back to room temperature and measured for color difference. Specifically, the oral compositions after storage were each placed in a polystyrene container to a height of 2 cm and photographed on a white board with an FD-5 fluorescence spectrodensitometer (produced by Konica Minolta, Inc.). The shooting conditions were the following: constant lighting, shutter speed, aperture, and focal length. Each value of the $L^*a^*b^*$ color system was measured at 6 measurement points, and the average was determined. The average was then applied to the following formula to determine the whiteness of each oral composition.

$$\text{Whiteness} = \sqrt{(L^*)^2 + (a^*)^2 + (b^*)^2}$$

"(value)^2" indicates the square of the value.

TABLE 4B

|  | Comparative Example 1a' | Example 1a' | Comparative Example 2a' |
| --- | --- | --- | --- |
| Silica |  | 10 |  |
| HAp produced in accordance with the procedure of Example 1 | — | 5 | — |
| Commercially Available HAp | — | — | 5 |
| Potassium Nitrate | | 5 | |
| Aluminum Lactate | | 2 | |
| 48% Caustic Soda | | 1.04 | |
| Water | | 20.2 | |
| Saccharin Sodium | | 0.12 | |
| Polyoxyethylene Hydrogenated Castor Oil | | 1 | |
| Sorbitol | | 13.2 | |
| Methyl Benzoate | | 0.2 | |
| Sodium Carboxymethyl Cellulose | | 1.8 | |
| 10% Aqueous Solution of Sodium Lauryl Sulfate | | 1 | |
| Flavoring Agent | | 0.98 | |
| Glycerol | | Balance | |
| Water Separation Percentage 55° C., 4M | 12% | 0% | 17% |
| Whiteness 55° C., 4M | 3.24 | 35.21 | 37.52 |

The results indicate that the oral composition containing specific hydroxyapatite particles and silica obtained in the Example exhibited excellent water separation percentage and whiteness in storage at a high temperature.

Test Example 8: Study on Yellowing of Oral Composition Due to Aluminum Lactate

Oral compositions were prepared by using hydroxyapatite particles obtained in the same manner as in Example 1 (HAp produced in accordance with the procedure of Example 1) or commercially available hydroxyapatite particles (commercially available HAp, produced by Tomita Pharmaceutical Co., Ltd.; commercially available hydroxyapatite different from the above reagent HAp) with aluminum lactate. Specifically, oral compositions were prepared by mixing the components shown in Table 5. The value of each component shown in Table 5 is indicated in mass %. HAp produced in accordance with the procedure of Example 1 and commercially available HAp were measured for X-ray crystal diffraction in the same manner as in Example 1. The ratio of the diffraction peak intensity of the (211) plane around 2θ=32° to the diffraction peak intensity of the (002) plane around 2θ=26° was 1.44 in the HAp produced in accordance with the procedure of Example 1 and 2.72 in the commercially available HAp. Caustic soda was also added to the compositions containing aluminum lactate to adjust the pH to around 7.

TABLE 5

|  | Comparative Example 1c | Example 1c | Comparative Example 2c | Comparative Example 1d | Example 1d | Comparative Example 2d |
|---|---|---|---|---|---|---|
| Aluminum Lactate | — | — | — | — | 2 | — |
| HAp produced in accordance with the procedure of Example 1 | — | 5 | — | — | 5 | — |
| Commercially Available HAp | — | — | 5 | — | — | 5 |
| 48% Caustic Soda | — | — | — | — | 1.04 | — |
| Water | 20.2 | | | | | |
| Saccharin Sodium | 0.12 | | | | | |
| Polyoxyethylene Hydrogenated Castor Oil | 1 | | | | | |
| 70% Sorbitol Liquid | 13.2 | | | | | |
| Methyl Benzoate | 0.2 | | | | | |
| Sodium Alginate | 1.7 | | | | | |
| Flavoring Agent | 0.98 | | | | | |
| Glycerol | Balance | | | | | |

Figure 29:
FIG. 29 shows the b* value of each oral composition in Comparative Example 1c, Example 1c, Comparative Example 2c, Comparative Example 1d, Example 1d, and Comparative Example 2d in the order from the left.

At least 60 mL of each obtained oral composition was placed in a colorless transparent glass container (produced by Hakuyo Glass Co., Ltd.) and stored at 55° C. in a dark room for 3 months. Thereafter, the oral compositions were measured for color difference as described below. The oral compositions after storage were each placed in a polystyrene container to a height of 2 cm and photographed on a white board with an FD-5 fluorescence spectrodensitometer (produced by Konica Minolta, Inc.). The shooting conditions were the following: constant lighting, shutter speed, aperture, and focal length. The b* value of the L*a*b* color system was measured at 6 measurement points, and the average was determined to use it as an index for evaluating the change in color to yellow (yellowing). FIG. 29 shows the results (the b* value of each oral composition). From the left, the six bars in FIG. 29 show the b* value of Comparative Example 1c, Example 1c, Comparative Example 2c, Comparative Example 1d, Example 1d, and Comparative Example 2d.

The results indicate that yellowing was suppressed in the oral compositions containing hydroxyapatite particles and aluminum lactate.

Test Example 9: Study on Effect of Oral Composition Containing Hydroxyapatite Particles and Fluorine Compound Oral compositions were prepared by using hydroxyapatite particles obtained in the same manner as in Example 1 (HAp produced in accordance with the procedure of Example 1) or commercially available hydroxyapatite particles (commercially available HAp, produced by Tamita Pharmaceutical Co., Ltd.; commercially available hydroxyapatite different from the above reagent HAp) with sodium monofluorophosphate or sodium fluoride. Specifically, oral compositions were prepared by mixing the components shown in Table 6. The value of each component shown in Table 6 is indicated in mass %. The HAp produced in accordance with the procedure of Example 1 and commercially available HAp were measured for X-ray crystal diffraction in the same manner as in Example 1. The ratio of the diffraction peak intensity of the (211) plane around 2θ=320 to the diffraction peak intensity of the (002) plane around 2θ=26° was 1.44 in the HAp produced in accordance with the procedure of Example 1 and 2.72 in the commercially available HAp.

TABLE 6

|  | Comparative Example 1e | Example 1e | Comparative Example 2e | Comparative Example 1f | Example 1f | Comparative Example 2f | Comparative Example 1g | Example 1g | Comparative Example 2g |
|---|---|---|---|---|---|---|---|---|---|
| Sodium Monofluorophosphate | — | — | | | 1.08 | | | | |
| Sodium Fluoride | — | — | | | | | | 0.31 | |
| HAp produced in accordance with the procedure of Example 1 | — | 5 | — | — | 5 | — | — | 5 | — |
| Commercially Available HAp | — | — | 5 | — | — | 5 | — | — | 5 |
| Water | 20.2 | | | | | | | | |
| Saccharin Sodium | 0.12 | | | | | | | | |
| Polyoxyethylene Hydrogenated Castor Oil | 1 | | | | | | | | |
| 70% Sorbitol Liquid | 13.2 | | | | | | | | |
| Methyl Benzoate | 0.2 | | | | | | | | |
| Sodium Carboxymethyl Cellulose | 1.8 | | | | | | | | |
| Xanthan Gum | 0.5 | | | | | | | | |
| Flavoring Agent | 0.98 | | | | | | | | |
| Glycerol | Balance | | | | | | | | |

Figure 30:
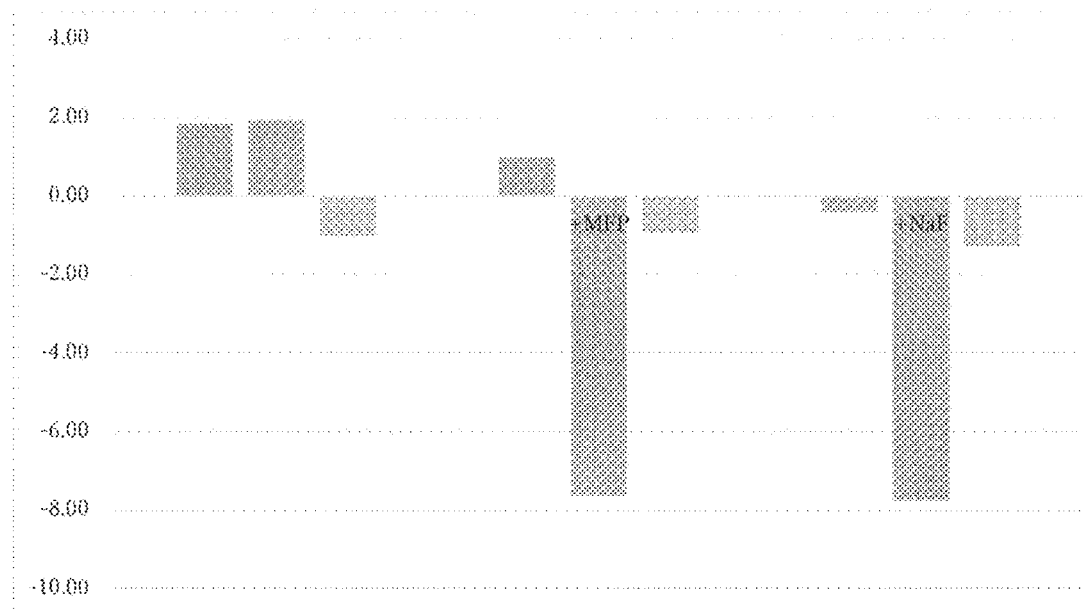
FIG. 30 shows the b* value of each oral composition in Comparative Example 1e, Example 1e, Comparative Example 2e, Comparative Example 1f, Example 1f, Comparative Example 2f, Comparative Example 1g, Example 1g, and Comparative Example 2g in the order from the left.

25 g of each obtained oral composition was placed in a laminate tube (aperture diameter: 8 mm) and stored at 55° C. in a dark room for 6 months. The oral compositions were brought back to room temperature and then measured for color difference in the following manner. The oral compositions after storage were each placed in a polystyrene container to a height of 2 cm and photographed on a white board with an FD-5 fluorescence spectrodensitometer (produced by Konica Minolta, Inc.). The shooting conditions were the following: constant lighting, shutter speed, aperture, and focal length. The b* value of the L*a*b* color system was measured at 6 measurement points, and the average was determined to use it as an index for evaluating the change in color to yellow (yellowing). FIG. 30 shows the results (the b* value of each oral composition). From the left, the nine bars in FIG. 30 show the b* value of Comparative Example 1e, Example 1e, Comparative Example 2e, Comparative Example 1f, Example 1f, Comparative Example 2f, Comparative Example 1g, Example 1g, and Comparative Example 2g.

The results indicate that yellowing was synergistically suppressed in the oral compositions containing hydroxyapatite particles and a fluorine compound.

Test Example 10: Study on Effect of Oral Composition Containing Hydroxyapatite Particles and Tin Fluoride Oral compositions were prepared by using hydroxyapatite particles obtained in the same manner as in Example 1 (HAp produced in accordance with the procedure of Example 1) or commercially available hydroxyapatite particles (commercially available HAp, produced by Tomita Pharmaceutical Co., Ltd.; commercially available hydroxyapatite different from the above reagent HAp) with tin fluoride (stannous fluoride). Specifically, oral compositions were prepared by mixing the components shown in Table 7. The value of each component shown in Table 7 is indicated in masse. The HAp produced in accordance with the procedure of Example 1 and commercially available HAp were measured for X-ray crystal diffraction in the same manner as in Example 1. The ratio of the diffraction peak intensity of the (211) plane around 2θ=320 to the diffraction peak intensity of the (002) plane around 2θ=26° was 1.44 in the HAp produced in accordance with the procedure of Example 1 and 2.72 in the commercially available HAp.

25 g of each obtained oral composition was placed in a laminate tube (aperture diameter: 8 mm) and stored at room temperature (about 25° C.) or 55° C. in a dark room for 5 months. The oral compositions stored at 55° C. were brought back to room temperature. The oral compositions were pushed out; about 0.5 g of each oral composition was weighed with an electronic balance and placed on a toothbrush (G.U.M Dental Brush #211M; Sunstar Inc.). The period of time was measured until the oral composition dropped off the toothbrush after the toothbrush was turned over at a height of 2.5 am so that the bristles faced downward. The period of time was determined to be the time required for dropping off. Table 7 also shows the results of this study.

After storage at room temperature or 55° C. (after the oral compositions stored at 55° C. were brought back to room temperature), the oral compositions were each pushed out by a length of 2 cm on coarse paper and allowed to stand at room temperature for 5 minutes. Thereafter, the length of the oral compositions was measured, and the broadening percentage (%) was determined from the following formula. Table 7 also shows the results.

The broadening percentage (%)=(the length of an oral composition after being allowed to stand for 5 minutes)/(the length of the oral composition pushed out on coarse paper)×100

As is clear from the formula, when the length of the oral composition after being allowed to stand does not change, the broadening percentage (t) is 100%. The greater the length, the higher the broadening percentage.

Additionally, the oral compositions immediately after preparation were warmed in a thermostatic bath at 30° C. for 30 minutes, and then the pH of the oral compositions was measured with a glass-electrode pH meter (LAQUA F-72, produced by Horiba, Ltd.). Table 7 also shows the measured pH values.

TABLE 7

| | | Comparative Example 1h | Example 1h | Comparative Example 2h | Comparative Example 1i | Example 1i | Comparative Example 2i |
|---|---|---|---|---|---|---|---|
| Tin Fluoride | | | | | 0.4 | | |
| HAp produced in accordance with the procedure of Example 1 | | — | 5 | — | — | 5 | — |
| Commercially Available HAp | | — | — | 5 | — | — | 5 |
| 48% Caustic Soda | | | | — | | 0.34 | |
| Water | | | | 20.2 | | | |
| Silicio Anhydride | | | | 15 | | | |
| Saccharin Sodium | | | | 0.12 | | | |
| Polyoxyethylene Hydrogenated Castor Oil | | | | 1 | | | |
| 70% Sorbitol Liquid | | | | 13.2 | | | |
| Methyl Benzoate | | | | 0.2 | | | |
| Sodium Carboxymethyl Cellulose | | | | 1.8 | | | |
| Flavoring Agent | | | | 0.98 | | | |
| Glycerol | | | | Balance | | | |
| PH | | 1.81 | 5.23 | 4.96 | 6.72 | 1.21 | 6.88 |
| Room Temperature | Broadening Percentage (%) | 140% | 100% | 120% | 120% | 100% | 100% |
| | Time Required for Dropping Off (seconds) | 30 | >180 | 10 | 15 | >180 | 100 |
| 55° C. | Broadening Percentage (%) | 125% | 100% | 120% | 140% | 100% | 140% |
| | [Time Required for Dropping Off (seconds) | 5 | >180 | >180 | 20 | >180 | 30 |

The results indicate that while tin fluoride-containing oral compositions, which are not so good in shape retention, do not exhibit improved shape retention as much when known hydroxyapatite (commercially available product) is added thereto, shape retention is remarkably improved by adding specific hydroxyapatite obtained in the Example. Additionally, while a tin fluoride-containing oral composition with a higher pH exhibited deteriorated shape retention when known hydroxyapatite was added, a tin fluoride-containing oral composition to which specific hydroxyapatite obtained in an Example was added exhibited improved shape retention regardless of the pH.

Test Example 11

Oral compositions were prepared by using hydroxyapatite particles obtained in the same manner as in Example 1 (HAp produced in accordance with the procedure of Example 1) or commercially available hydroxyapatite particles (commercially available HAp, produced by Tomita Pharmaceutical Co., Ltd.; commercially available hydroxyapatite different from the above reagent HAp) with sodium monofluorophosphate or sodium fluoride. Specifically, oral compositions were prepared by mixing the compositions shown in Table 8. The value of each component in Table 8 is indicated in mass %. The HAp produced in accordance with the procedure of Example 1 and commercially available HAp were the same as those used in Test Example 7, and measured for X-ray crystal diffraction in the same manner as in Example 1. The ratio of the diffraction peak intensity of the (211) plane around $2\theta=32°$ to the diffraction peak intensity of the (002) plane around $2\theta=26°$ was 1.44 in the HAp produced in accordance with the procedure of Example 1 and 2.72 in the commercially available HAp.

The fluorine content (ppm) of oral compositions was determined in accordance with the following procedure immediately after production of the oral compositions and after 25 g of each oral composition was placed in a laminate tube (aperture diameter: 8 mm) and stored at 55° C. for 2 months in a dark room. About 0.5 g of a specimen was precisely weighed, and 5 mL of a 2 mol/L perchloric acid test solution was added thereto. After the mixture was shaken well, the mixture was heated for 5 minutes. After cooling, water was added to form a precise volume of 100 mL. 15 mL of an acetate buffer (pH 5.3) was precisely added to 5 mL of this liquid, thereby preparing a sample solution. The fluorine content of the sample solution and a separately prepared fluorine standard solution was determined by reading their electrical potential by using fluorine test method 2 (ion electrode method) described in the Japanese Standards of Quasi-Drug Ingredients 2006.

Additionally, the percentage of the change in fluorine content from immediately after production was determined by using the following formula.

Percentage of the change in fluorine content=(the fluorine content after storage at 55° C. for 2 months)/(the fluorine content immediately after production)

The percentage of the change in fluorine content of 90% or more was rated as "✓," with less than 90% rated as "x."

TABLE 8

|  | Comparative Example 1-1 | Example 1-1 | Comparative Example 1-2 | Comparative Example 2-1 | Example 2-1 | Comparative Example 2-2 |
|---|---|---|---|---|---|---|
| Potassium Nitrate |  |  |  |  | 5 |  |
| Sodium Fluoride |  |  |  | 0.31 |  |  |
| Sodium Monofluorophosphate |  |  |  | — |  |  |
| HAp produced in accordance with the procedure of Example 1 | — | 5 | — | — | 5 | — |
| Commercially Available HAD | — | — | 5 | — | — | 5 |
| Calcium Carbonate | 15 | | | | | |
| Water | 20.2 | | | | | |
| Saccharin Sodium | 0.12 | | | | | |
| Sorbitol | 13.2 | | | | | |
| Methyl Benzoate | 0.2 | | | | | |
| Flavoring Agent | 0.98 | | | | | |
| Glycerol | Balance | | | | | |
| Initial Point (ppm) | 1447 | 1400 | 1432 | 1320 | 1342 | 1329 |
| 55° C., 2M (ppm) | 1368 | 1467 | 1386 | 972 | 1290 | 987 |
| Percentage of Change (55° C., 2M/initial point) | 95% | 105% | 97% | 74% | 96% | 74% |
|  | ✓ | ✓ | ✓ | ✓ | ✓ | x |

|  | Comparative Example 3-1 | Example 3-1 | Comparative Example 3-2 | Comparative Example 4-1 | Example 4-1 | Comparative Example 4-2 |
|---|---|---|---|---|---|---|
| Potassium Nitrate |  |  |  |  | 5 |  |
| Sodium Fluoride |  |  |  | — |  |  |
| Sodium Monofluorophosphate |  |  | 1.08 |  |  |  |
| HAp produced in accordance with the procedure of Example 1 | — | 5 | — | — | 5 | — |
| Commercially Available HAD | — | — | 5 | — | — | 5 |
| Calcium Carbonate | 15 | | | | | |
| Water | 20.2 | | | | | |
| Saccharin Sodium | 0.12 | | | | | |
| Sorbitol | 13.2 | | | | | |
| Methyl Benzoate | 0.2 | | | | | |
| Flavoring Agent | 0.98 | | | | | |
| Glycerol | Balance | | | | | |
| Initial Point (ppm) | 1429 | 1421 | 1405 | 1359 | 1434 | 1422 |
| 55° C., 2M (ppm) | 1433 | 1460 | 1386 | 1355 | 1364 | 1243 |
| Percentage of Change (55° C., 2M/initial point) | 100% | 103% | 99% | 100% | 95% | 87% |
|  | ✓ | ✓ | ✓ | ✓ | ✓ | x |

Table 8 also shows the results.

The results indicate that while the stability of the contained fluorine is decreased in oral compositions containing potassium nitrate in addition to known hydroxyapatite particles and a fluorine compound, the use of the HAp particles produced in accordance with the procedure of Example 1 as hydroxyapatite particles can suppress the decrease in the stability of fluorine in even an oral composition further containing a fluorine compound and potassium nitrate.

The invention claimed is:

1. An oral composition comprising hydroxyapatite particles, wherein the hydroxyapatite particles have a ratio of a diffraction peak intensity around $2\theta=32°$ to a diffraction peak intensity around $2\theta=26°$ of 0.8 to 1.6 in an x-ray powder diffraction pattern as measured with a CuKα characteristic X-ray, wherein the hydroxyapatite particles have a Ca/P molar ratio of less than 1.67, wherein the hydroxyapatite particles have a median diameter of 5 μm or less, wherein the hydroxyapatite particles have a specific surface area of 30 to 200 m$^2$/g, wherein the hydroxyapatite particles are each an aggregate of plate-like crystals of hydroxyapatite, and wherein the oral composition further comprises potassium nitrate and/or aluminum lactate.

2. The oral composition according to claim 1, wherein the hydroxyapatite particles have a ratio of a diffraction peak intensity around $2\theta=34°$ to a diffraction peak intensity around $2\theta=32°$ of 1 or less in an x-ray powder diffraction pattern as measured with a CuKα characteristic X-ray.

3. The oral composition according to claim 1, further comprising a fluorine compound.

4. The oral composition according to claim 1, further comprising tin fluoride.

5. The oral composition according to claim 1, further comprising silica.

6. A method for improving hypersensitivity comprising administering the oral composition according to claim 1.

7. The oral composition according to claim 1, wherein the hydroxyapatite particles have a specific surface area of 30 to 100 m$^2$/g.

8. The oral composition according to claim 1, wherein the hydroxyapatite particles have a Ca/P molar ratio of less than 1.50.

9. The oral composition according to claim 1, wherein the hydroxyapatite particles have a specific surface area of 30 to 100 m$^2$/g and a Ca/P molar ratio of less than 1.

* * * * *